United States Patent [19]
Zadno-Azizi et al.

[11] Patent Number: 6,050,972
[45] Date of Patent: Apr. 18, 2000

[54] GUIDEWIRE INFLATION SYSTEM

[75] Inventors: Gholam-Reza Zadno-Azizi, Newark; April A. Marano-Ford, Palo Alto; Celso J. Bagaoisan, Union City; Jefferey C. Bleam, Boulder Creek; Isaac J. Kim, San Jose; Jeffrey F. Field, Camarillo; Roy Leguidleguid, Union City; Mukund Patel, San Jose; George Tsai, Sunnyvale, all of Calif.

[73] Assignee: PercuSurge, Inc., Sunnyvale, Calif.

[21] Appl. No.: 08/975,723

[22] Filed: Nov. 20, 1997

Related U.S. Application Data

[63] Continuation-in-part of application No. 08/812,139, Mar. 6, 1997, abandoned, which is a continuation-in-part of application No. 08/650,464, May 20, 1996, abandoned.

[51] Int. Cl.[7] .................................................. A61M 29/00
[52] U.S. Cl. ................. 604/97; 604/96; 606/194
[58] Field of Search ................. 604/96, 97, 98, 604/99, 65, 95; 606/194, 191

[56] References Cited

U.S. PATENT DOCUMENTS

| | | |
|---|---|---|
| 3,144,868 | 8/1964 | Jascalevich . |
| 3,982,544 | 9/1976 | Dyck . |
| 4,205,683 | 6/1980 | O'Neill . |
| 4,205,691 | 6/1980 | Patel . |
| 4,333,452 | 6/1982 | Au . |
| 4,445,892 | 5/1984 | Hussein et al. . |
| 4,468,216 | 8/1984 | Muto . |
| 4,511,354 | 4/1985 | Sterling . |
| 4,573,966 | 3/1986 | Weikl et al. . |
| 4,639,247 | 1/1987 | Bokros . |
| 4,748,982 | 6/1988 | Horzewski et al. . |
| 4,803,999 | 2/1989 | Liegner . |
| 4,946,466 | 8/1990 | Pinchuk et al. . |
| 4,964,409 | 10/1990 | Tremulis . |
| 4,968,306 | 11/1990 | Huss et al. . |
| 5,059,178 | 10/1991 | Ya . |
| 5,156,596 | 10/1992 | Balbierz et al. . |
| 5,163,906 | 11/1992 | Ahmadi . |
| 5,167,239 | 12/1992 | Cohen et al. . |
| 5,201,712 | 4/1993 | Bryant . |
| 5,219,329 | 6/1993 | Fischell et al. . |
| 5,322,508 | 6/1994 | Viera . |
| 5,364,376 | 11/1994 | Horzewski et al. . |
| 5,376,077 | 12/1994 | Gomringer . |
| 5,423,742 | 6/1995 | Theron . |
| 5,439,000 | 8/1995 | Gunderson et al. . |
| 5,449,343 | 9/1995 | Samson et al. . |
| 5,462,529 | 10/1995 | Simpson et al. . |
| 5,478,331 | 12/1995 | Heflin et al. . |
| 5,484,418 | 1/1996 | Quiachon et al. . |
| 5,500,180 | 3/1996 | Anderson et al. . |
| 5,807,330 | 9/1998 | Teitelbaum . |

FOREIGN PATENT DOCUMENTS

| | | |
|---|---|---|
| 0 547 358 | 11/1992 | European Pat. Off. . |
| 0 710 490 A2 | 5/1996 | European Pat. Off. . |
| 2 139 725 | 4/1984 | United Kingdom . |
| WO 96/15824 | 5/1996 | WIPO . |
| WO 97/27896 | 8/1997 | WIPO . |

*Primary Examiner*—Corrine McDermott
*Assistant Examiner*—Kent Gring
*Attorney, Agent, or Firm*—Knobbe, Martens, Olson & Bear, LLP

[57] ABSTRACT

Disclosed herein is a low profile catheter valve comprising a movable sealer portion positioned within the inflation lumen of a catheter. The sealer portion forms a fluid tight seal with the inflation lumen by firmly contacting the entire circumference of a section of the inflation lumen. The sealer portion may be positioned proximally of a side-access inflation port on the catheter, to establish an unrestricted fluid pathway between the inflation port and an inflatable balloon on the distal end of the catheter. As desired, the clinician may move the sealer portion to a position distal of the inflation port, thereby preventing any fluid from being introduced into or withdrawn from the balloon via the inflation port. Also disclosed herein is an inflation adaptor for moving the sealer portion within the catheter to establish or close the fluid pathway between the inflation port and the inflatable balloon.

20 Claims, 16 Drawing Sheets

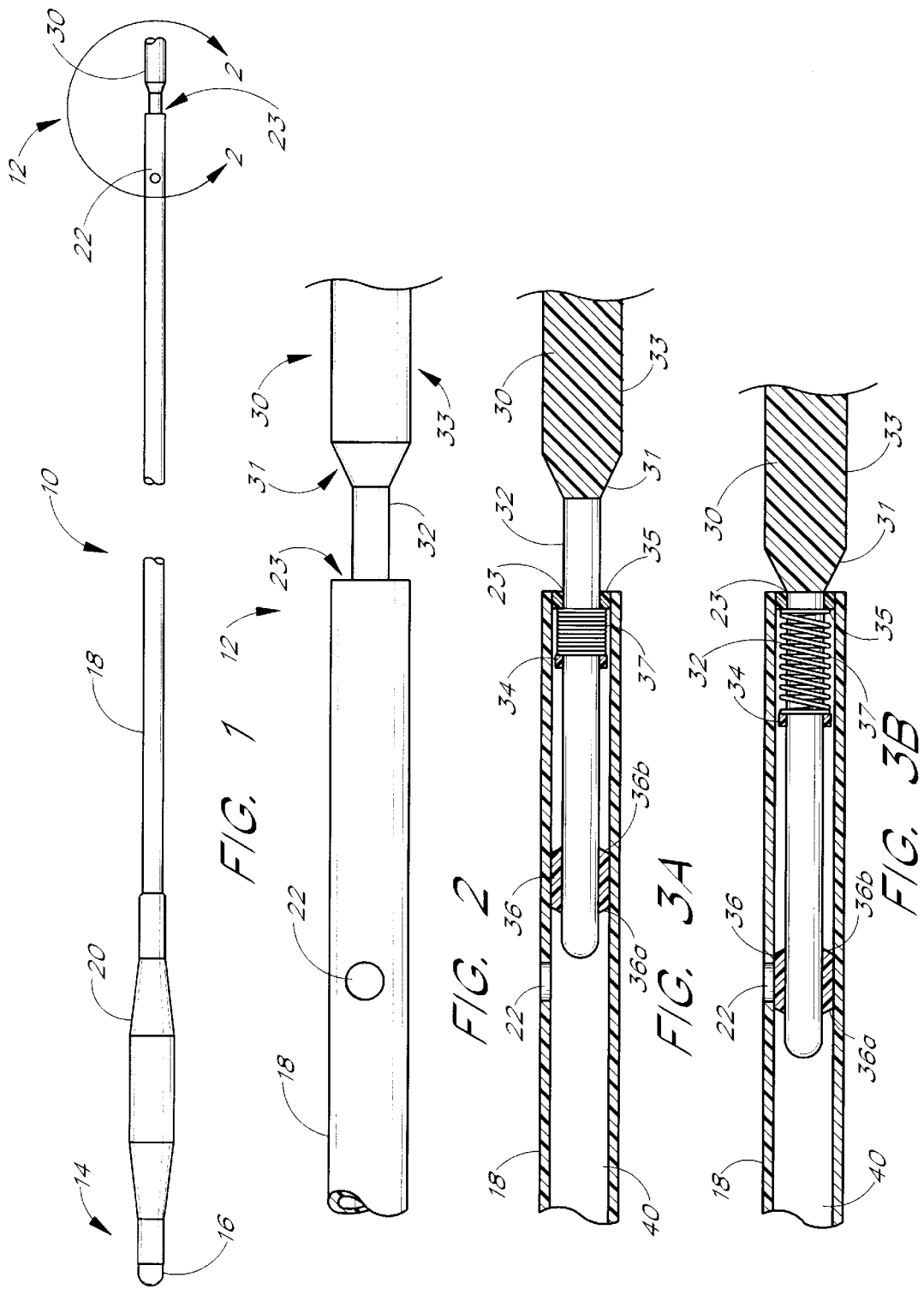

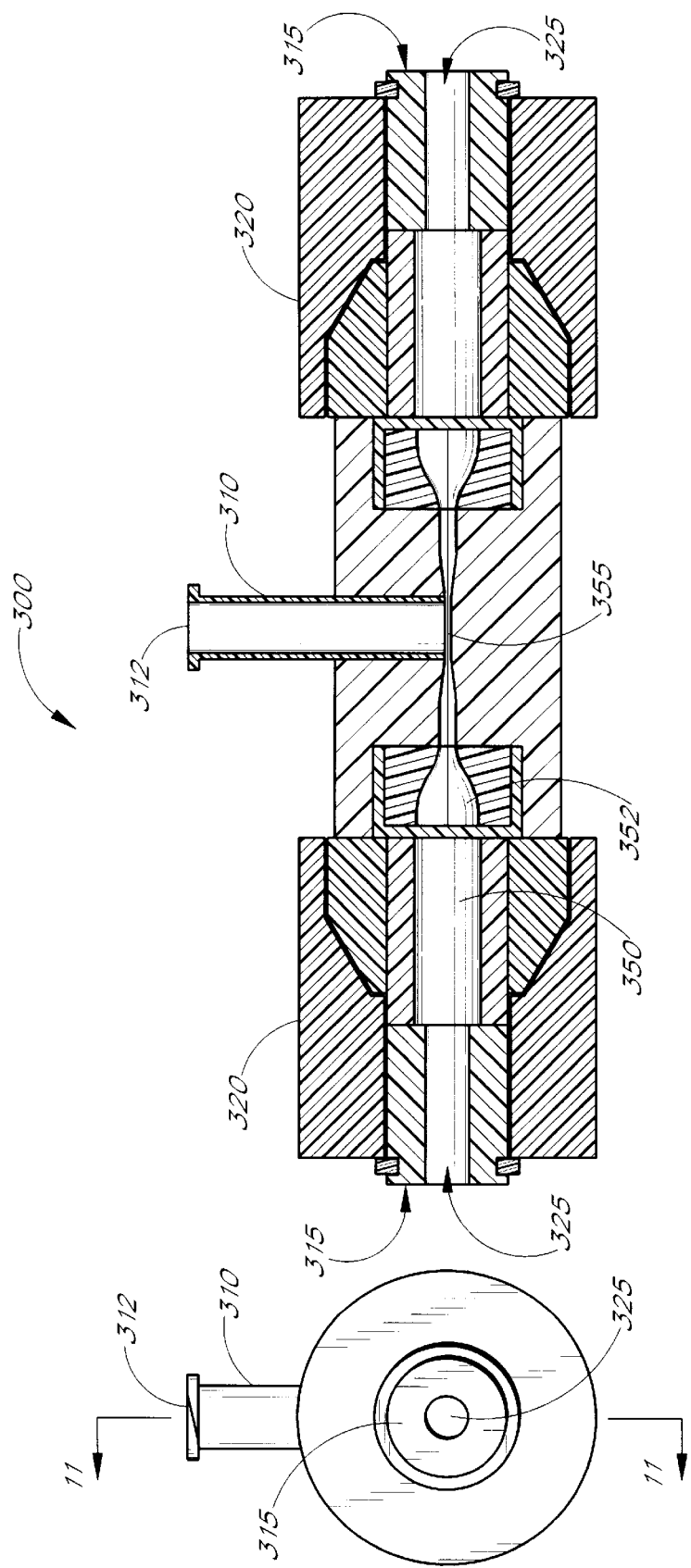

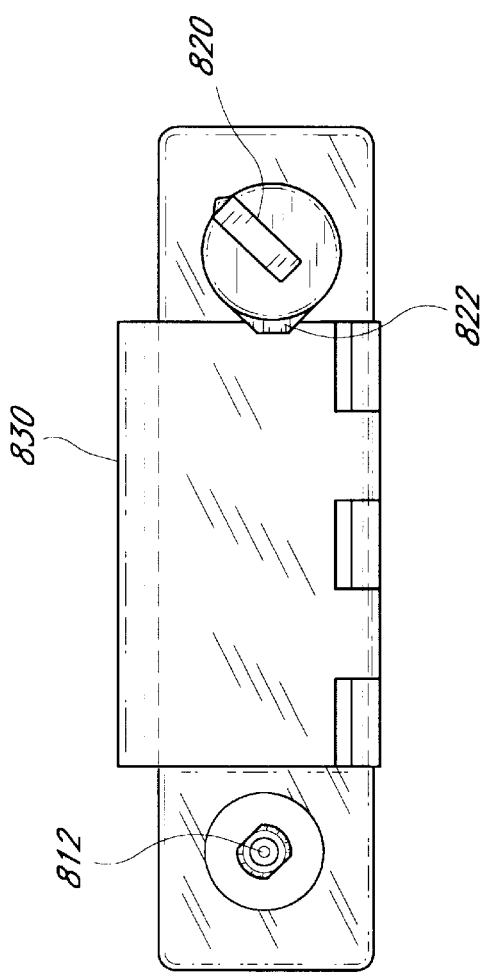
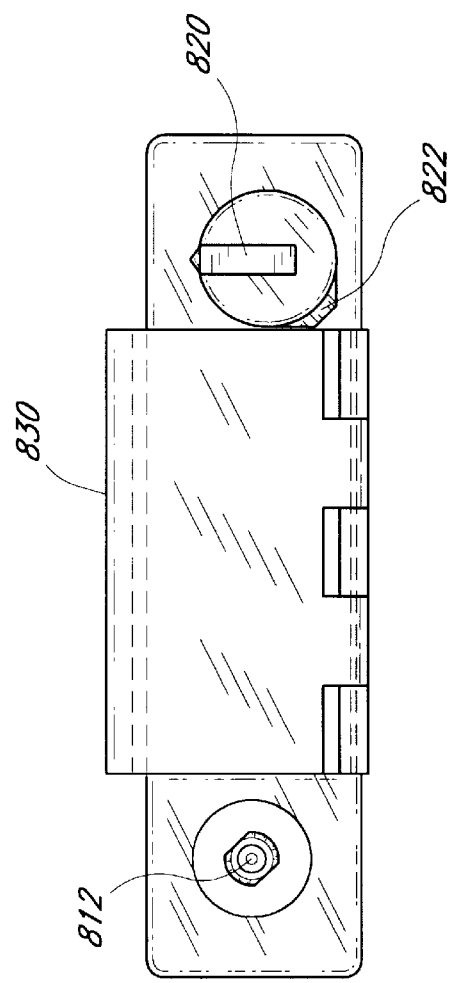
FIG. 18A
FIG. 18B

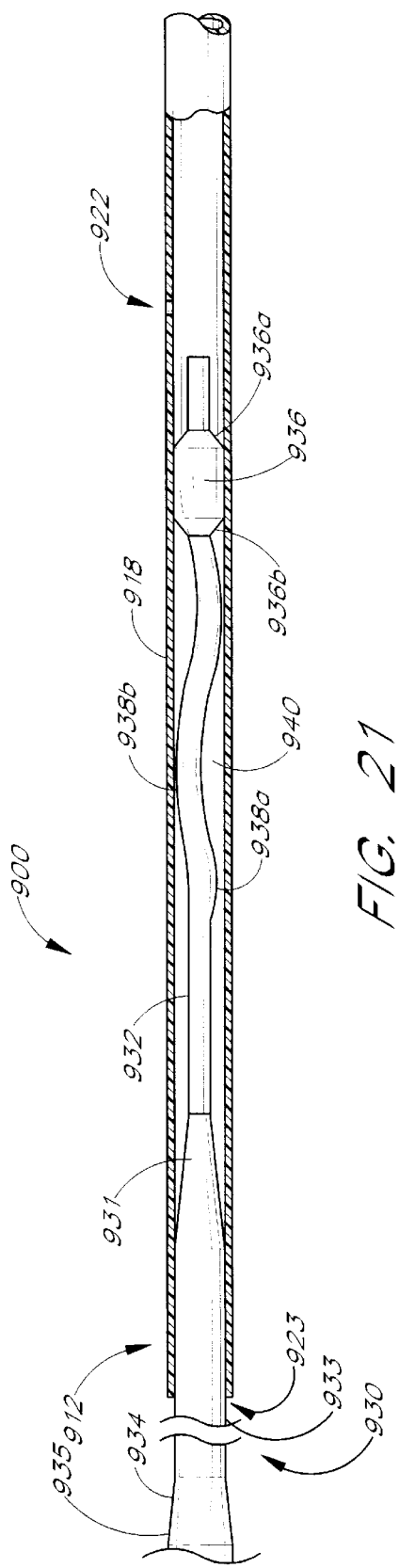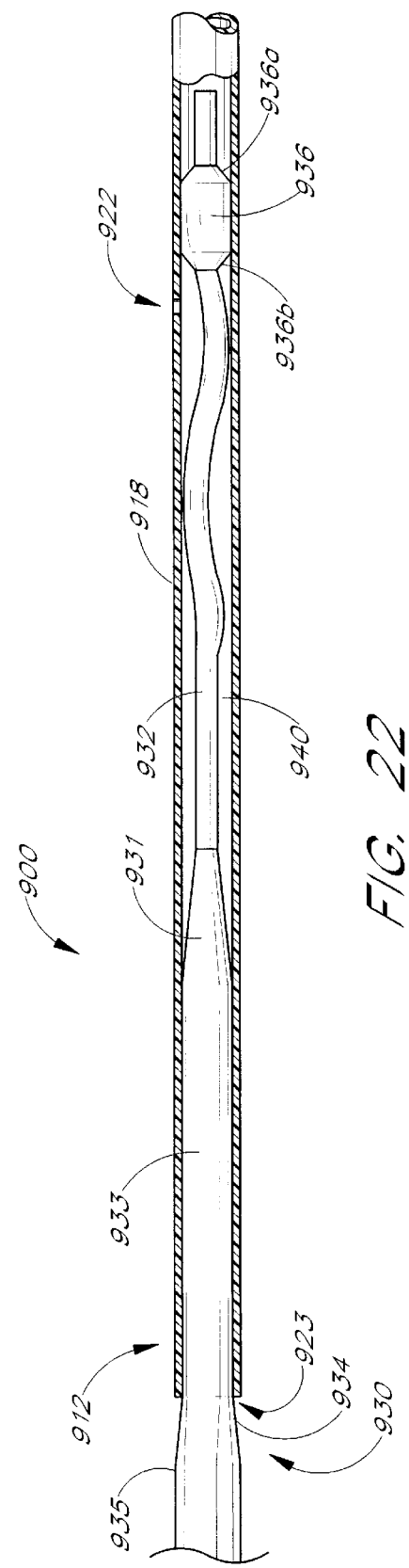

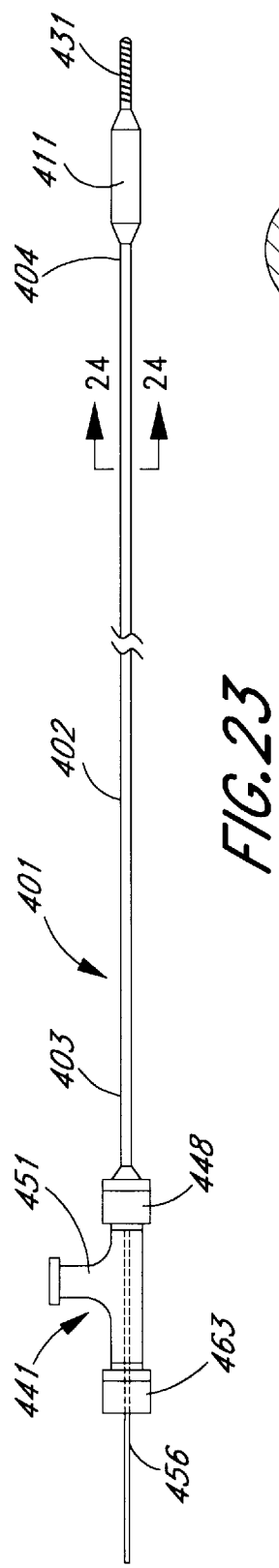
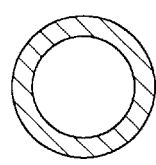
FIG. 24
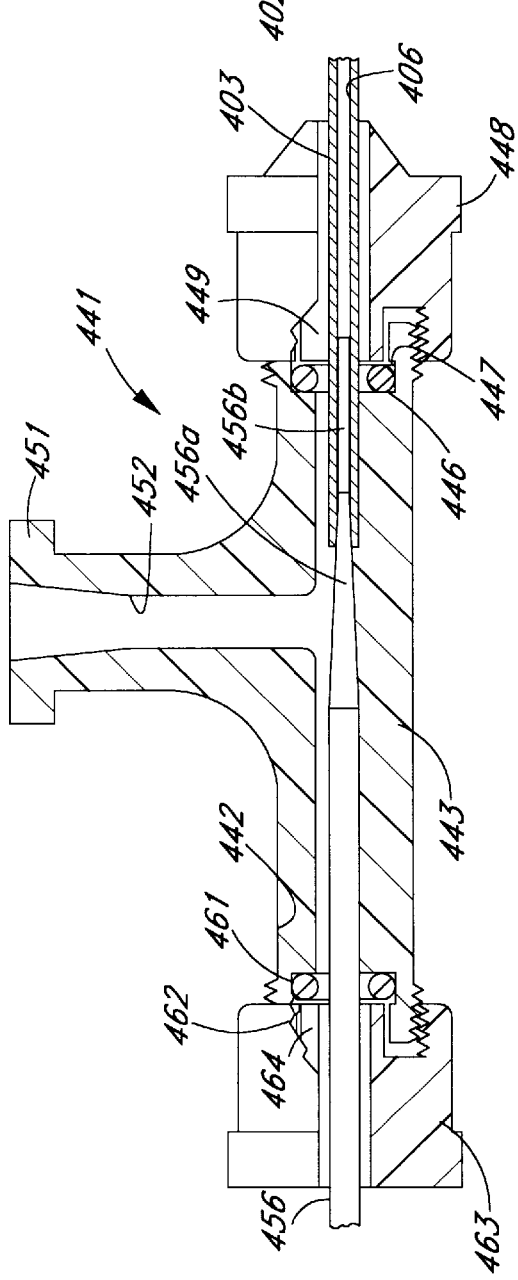

GUIDEWIRE INFLATION SYSTEM

CROSS-REFERENCE TO RELATED APPLICATIONS

The present application is a continuation-in-part of application Ser. No. 08/812,139, filed Mar. 6, 1997 now abandoned, which is continuation-in-part of application Ser. No. 08/650,464 filed on May 20, 1996, now abandoned, the entirety of both of which are hereby incorporated by reference.

BACKGROUND OF THE INVENTION

The present invention generally relates to catheters, and in particular, to a detachable inflation adaptor for a catheter having a low profile valve which may be opened to permit inflation or deflation of a catheter balloon, such as an occlusion balloon, and which may be closed when it is desirable to maintain the catheter balloon in an inflated state.

Guidewires are conventionally used to guide the insertion of various medical instruments, such as catheters, to a desired treatment location within a patient's vasculature. In a typical procedure, the clinician forms an access point for the guidewire by creating an opening in a peripheral blood vessel, such as the femoral artery. The highly flexible guidewire is then introduced through the opening into the peripheral blood vessel, and is then advanced by the clinician through the patient's blood vessels until the guidewire extends across the vessel segment to be treated. Various treatment catheters, such as a balloon dilatation catheter for a percutaneous transluminal coronary angioplasty, may then be inserted over the guidewire and similarly advanced through vasculature until they reach the treatment site.

In certain treatment procedures, it is desirable to successively introduce and then remove a number of different treatment catheters over a guidewire that has been placed in a particular location. In other words, one treatment catheter is "exchanged" for another over a single guidewire. Such an exchange typically involves withdrawing the treatment catheter over the guidewire until the treatment catheter is fully removed from the patient and the portion of the guidewire which extends from the patient. The guidewire is then available to act as a guide for a different treatment catheter.

In emboli containment devices, which typically utilize two occlusion balloons to form a chamber, it may be desirable to exchange therapeutic catheters without deflating the occlusion balloons. Further, it is sometimes advantageous to anchor the guidewire during the exchange. As can be readily appreciated, the withdrawal of treatment catheters over a placed guidewire may result in the guidewire being displaced from its position. To overcome this difficulty, the prior art has developed "anchorable" guidewires, which generally feature some structure on their distal ends to releasably secure the guidewire at a particular location in the patient for the duration of the medical procedure. One such anchorable guidewire is disclosed in U.S. Pat. No. 5,167,239 to Cohen et al., which discloses a hollow guidewire with an inflation lumen and an expandable balloon on its end. The Cohen guidewire is positioned in the same manner as a conventional wire guidewire, but once placed, its expandable balloon is inflated to contact the surrounding vasculature, thereby preventing the guidewire from being displaced.

Because a permanent inflation manifold, of the type used with conventional catheters having an inflatable balloon, would prevent other catheters from being inserted over the Cohen guidewire, the Cohen device also includes a removable inflation manifold, and a check valve to maintain the balloon in the inflated state when the manifold is removed. The check valve apparatus used by the Cohen device is relatively bulky, and is described as having an outer diameter in its preferred embodiment of 0.0355 inches. Consequently, any treatment catheter intended to be inserted over the Cohen device must have an interior guidewire lumen larger than the outer diameter of the Cohen valve, which for the preferred embodiment, requires an interior lumen with a diameter of more than 0.0355 inches.

As is readily appreciated by those of skill in the art, increasing the interior lumen size of a treatment catheter results in an increase in the outer diameter of the treatment catheter. For treatment procedures which take place in vasculature having a large blood vessel diameter, such as iliac arteries, a treatment catheter guidewire lumen of a size necessary to accommodate devices such as those described by Cohen would have little or no affect on the ability of the catheter to fit within the blood vessel. However, many blood vessels where it is desirable to apply catheter treatment are quite narrow. For example, the left coronary arteries are blood vessels having diameters ranging from 2 to 4 mm, and are susceptible to plaque. It would be desirable to use a catheter exchange treatment procedure, such as angioplasty, to treat such lesions, but the narrow diameter of the coronary vessels makes use of anchorable guidewires having large valve diameters impractical.

Consequently, there exists a need for a very low profile catheter valve which can be used with a hollow guidewire. Furthermore, there exists a need for a detachable inflation adaptor which can be used with such low profile valves to open and close them, and to apply inflation or deflation forces to the catheter balloons.

SUMMARY OF THE INVENTION

The present invention provides a catheter valve which is capable of very low profiles, and is especially advantageous for use with anchorable guidewires, as well as therapeutic or occlusion devices. By incorporating this into such devices, it is possible to manufacture anchorable guidewires and occlusion device catheters with outer diameters of 0.014 inches or smaller. Advantageously, by utilizing this valve in these catheters, clinicians will be able to use anchorable guidewires, therapeutic or occlusion device catheters in much narrower blood vessels than in the past.

The present invention also provides for a detachable inflation adaptor which can be used with catheters having these low profile valves. The adaptor can be attached tot he catheter to open the valve, and then apply inflation fluid to inflate the catheter balloon. Following this, the valve may then be closed and the adaptor removed, with the balloon remaining in its inflated state and the catheter now able to function as an anchored guidewire. When it is desired to deflate the balloon, the adaptor may be once again attached to the catheter, the valve opened, and the inflation fluid removed to deflate the balloon.

In one aspect of the present invention, there is provided a valve which comprises a flexible elongate tubular body having a proximal end and a distal end. The tubular body has a central lumen extending between the proximal and distal ends. The central lumen has an opening at the proximal end.

An expandable member, such as an inflatable balloon, is positioned on the distal end of the tubular body. The expandable member is in fluid communication with the central lumen. An access opening is provided on the tubular body. The access opening is in fluid communication with the central lumen to permit the expandable member to be actuated by pressurizing the access opening. The access opening may be the central lumen opening or a side-access port positioned on the tubular body at a point proximal to the distal end of the tubular body.

A sealing member is provided having a sealer portion which seals against a surface of the tubular body. The sealing portion of the sealing member is movable relative to the surface of the tubular body between two positions. In the first position, the sealer portion is positioned in contact with the tubular body surface at a location which blocks the flow of fluid to or from the expandable member through the access opening to maintain actuation of the expandable member. In the second position, the sealer portion is positioned at a location which permits the flow of fluid to or from the expandable member through the access opening to permit actuation or deactuation of the expandable member.

In one preferred embodiment, the sealing member has a portion which extends from the proximal end of the tubular body, and the application of a longitudinal force on the extending portion results in movement of the sealer portion in the direction of the applied force. In other embodiments, rotational forces may be used to move the sealing member.

There is also preferably provided a force-increasing structure which increases the longitudinal force which must be applied to the extending portion to move the sealer portion.

The sealer portion is preferably formed of a polymeric material, such as Pebax(TM), silicone, C-Flex(TM) or gels. The sealer portion is capable of withstanding pressures up to ten atmospheres and prevent substantially all fluid from passing to or from the expandable member through the access opening when the sealer portion is positioned distal to the access opening. The sealer portion is also capable of undergoing 10 valve-opening and closing cycles, and, at a pressure of ten atmospheres, still prevent substantially all fluid from passing to or from the balloon when the sealer portion is positioned distal to the access opening. At least a portion of the sealing member is selected from the group of metals consisting of nitinol, stainless steel, Elgiloy™ or combinations thereof.

Advantageously, the outer diameter of the tubular body is generally larger than the outer diameter of any portion of the sealing member or sealer portion. In some embodiments, the outer diameter of the tubular body is no greater than 0.038 inches, preferably no greater than 0.020 inches, and more preferably no greater than 0.014 inches. Other embodiments may have larger outer diameters for the tubular body. The tubular body may also have positive stops to prevent withdrawal of the sealing member from the opening.

There is also preferably provided in combination with this valve an inflation adaptor capable of receiving the valve. The inflation adaptor provides a fluid-tight chamber for introduction of a pressurized fluid to expand the expandable member.

In another aspect of the present invention, there is provided an apparatus, comprising a hollow metallic guidewire having a central lumen and a side-access port in fluid communication with the lumen. An inflatable balloon is mounted on the guidewire, the inflatable balloon being in fluid communication with the central lumen, such that fluid introduced through the side-access port can be used to inflate the balloon.

A valve is mounted to slide along a surface of the guidewire, the valve movable between first and second positions, one of the positions sealing the central lumen such that substantially no fluid may pass to or from the inflatable balloon by way of the side-access port.

Preferably, the hollow guidewire has an outer circumference defining a first value, and the movable valve has a circumference which is less than the first value. It is also preferred that the hollow guidewire have an outer circumference of 0.12 inches or less, more preferably 0.08 inches or less, and optimally 0.044 inches or less, and that the movable valve have a diameter not substantially larger than that of the hollow guidewire, and the valve seals against an interior surface of the hollow guidewire.

In another aspect of the present invention there is provided a low profile catheter valve which comprises a sealing member capable of being movably inserted through a proximal opening on a catheter into an inflation lumen of the catheter. The catheter has a side-access inflation port and an inflatable balloon in fluid communication with the side-access inflation port. A sealer portion is on the sealing member, the sealer portion being capable of forming a fluid tight seal with the entire circumference of a section of the lumen, such that substantially all fluid may not pass the sealer portion at normal balloon inflation pressures.

When the sealer portion is positioned within the lumen proximally of the side-access inflation port, an unrestricted fluid pathway is established between the side-access inflation port and the balloon. When the sealer portion is positioned within the lumen distally of the side-access inflation port, substantially all fluid may not pass to or from the balloon through the side-access inflation port at normal balloon inflation pressures.

In another aspect of the present invention, there is provided a method of inflating a catheter balloon. The first step of the method involves providing a tube having a proximal end and a distal end. The proximal end of the tube has an inflation opening to an inflation lumen and the distal end has an inflatable balloon in fluid communication with the inflation lumen. A pressurized inflation fluid is then introduced through the inflation opening to inflate the balloon. The inflation opening may then be sealed by moving a sealing member within the inflation lumen without reducing the pressure of the pressurized fluid, wherein the step of sealing is performed without substantial deflation of the inflated balloon. Finally, the pressure of the pressurized fluid may be reduced after completing the sealing step.

In another aspect of the present invention, there is provided a low profile catheter valve for use with an inflation adaptor. The valve comprises a sealing member capable of being movably inserted through a proximal opening on a catheter into an inflation lumen of the catheter. The catheter has an inflation opening and an inflatable balloon in fluid communication with the inflation opening. Indicia are present on the catheter and/or sealing member, the position of the indicia being such that the inflation opening is aligned with a fluid tight inflation chamber of the inflation adaptor when the catheter and sealing member are secured in the inflation adaptor.

A sealer portion is mounted on the sealing member. The sealer portion is capable of forming a fluid tight seal with the entire circumference of a section of the lumen, such that substantially all fluid may not pass the sealer portion at normal balloon inflation pressures. When the sealer portion is positioned proximally of the inflation opening, an unrestricted fluid pathway is established between the inflation opening and the balloon. When the sealer portion is positioned distally of the inflation opening, substantially all fluid may not pass to or from the balloon through the side-access inflation port.

In another aspect of the present invention, there is provided an inflation adaptor for introducing inflation fluid into an inflation port of an elongate tube. The inflation adaptor comprises a housing having first and second portions which interact to releasably retain a section of the tube therein. The housing has a chamber which receives the inflation port. An inflation inlet configured to be connected to a source of inflation fluid that supplies the fluid under pressure is positioned on the housing. The housing also has a seal which releasably seals the portions of the housing together, and provides a fluid pathway between the inflation inlet and the inflation port, so that fluid may be supplied to the inflation port under pressure. The seal is created by alignment of a first and second gasket on the housing portions. An actuator, mounted on the housing, drives a member within the tube to control fluid flow through the catheter inflation port. The actuator may control sliding panels which drive the tube members in some embodiments. Preferably, there are indicia on the elongate tube and housing which facilitate alignment of the catheter inflation port and the housing chamber.

In another aspect of the present invention, there is provided an inflation adaptor for introducing inflation fluid into an inflation port of an elongate tube. The inflation adaptor comprises a housing having first and second portions. The portions of the housing are relatively movably mounted to receive a section of the elongate tube which includes the inflation port. The housing also has an inflation chamber and an inflation inlet for introducing inflation fluid under pressure into the inflation chamber. The inflation chamber releasably seals the inflation port to the inflation inlet to form a fluid passage therebetween.

In another aspect of the present invention, there is provided an inflation adaptor for introducing inflation fluid into an inflation port of an elongate tube. The inflation adaptor comprises a housing having first and second portions. The two portions form a mouth for receiving a section of the tube which includes the inflation port. The mouth forms an opening having a height at least as great as the outer diameter of the tube such that the section of tube is insertable into the mouth from its side in a direction transverse to the longitudinal axis of the tube. The housing also has an inflation chamber and an inflation inlet for introducing inflation fluid under pressure into the inflation chamber. The inflation chamber releasably seals the inflation port to the inflation inlet to form a fluid passage there between.

In another aspect of the present invention, there is provided an inflation adaptor for introducing inflation fluid into an inflation port of an elongate tube. The tube has an inflatable member mounted thereon and an inflation lumen between the inflation port and the inflatable member. The adaptor has a housing configured to seal over the tubular body to create a fluid tight seal. An inflation inlet is on the housing, for establishing a fluid pathway between the inflation inlet and the inflation port to permit the inflatable member to be inflated. The housing is detachable from the tube without deflating the inflated inflatable member.

In another aspect of the present invention, there is provided an inflation adaptor for introducing inflation fluid into an inflation port of an elongate tube having an inflatable member mounted thereon and an inflation lumen between the inflation port and the inflatable member. The adaptor comprises a housing with an upper portion and a lower portion. The housing is configured to seal over the tube to create a fluid tight inflation chamber. The housing also has an inflation inlet and establishes a fluid pathway between the inflation inlet and the inflation port to permit the inflatable member to be inflated. The housing is detachable from the tube without deflating the inflated inflatable member.

A latch with a camming surface is on the housing, and is adapted to secure the housing upper portion to the housing lower portion. A cammed surface is on the housing upper, and is adapted to receive the camming surface. With this structure, when a user exerts a force on the latch to secure the upper portion to the lower portion, the camming surface cooperates with the cammed surface to provide a closing force on the upper and lower portions which is greater than the force exerted by the user.

In one preferred embodiment, the upper portion has a first gasket, and the lower portion has a second gasket, and the fluid tight inflation chamber is established when the gaskets are brought together and secured by the latch. Preferably, the upper portion has a movable panel with the movement being controlled by an actuator on the housing that is accessible to a clinician when the adaptor is in use. There is also a lower movable panel on the lower housing portion, which is capable of being moved in conjunction with the upper portion movable panel when the fluid tight inflation chamber is established.

In another prefered embodiment, a spring biased rod is connected to the lower portion movable panel, the spring biased rod defining the distance in at least one dimension that the upper portion movable panel and lower portion movable panel may travel when the fluid tight inflation chamber is established. The movable panel are preferably movable for a distance of greater than 1 mm, and more preferably for a distance of greater than 5 mm.

In another aspect of the present invention, there is provided a low profile catheter valve sealing member. The sealing member has an extension wire with a proximal end and a distal end. The extension wire tapers at the distal end. A connecting hypotube is attached to the extension wire proximal end. The connecting tube has a tapering distal end. A plug mandrel wire is attached to the hypotube distal end. A sealer portion is on the plug mandrel wire, the sealer portion being capable of forming a fluid tight seal with the entire circumference of a section of a catheter lumen.

In another aspect of the present invention, there is provided a low profile catheter valve sealing member for a catheter having a lumen with a first diameter. The sealing member has a first region having a diameter greater than the first diameter, and a tapering portion resulting in a second region with a diameter less than the first diameter. The second region is slidably inserted in the catheter lumen. A plug mandrel wire is connected to the second region at the distal end of the second region, the plug mandrel wire having a diameter smaller than the second region diameter. A sealer portion is on the plug mandrel wire, the sealer portion being capable of forming a fluid tight seal with the entire circumference of a section of a catheter lumen.

BRIEF DESCRIPTION OF THE DRAWINGS

FIG. 1 is a side view of a catheter incorporating the low profile valve of the present invention.

FIG. 2 is an enlarged view of the proximal portion of the catheter of FIG. 1, showing an exterior view of the catheter segment featuring the low profile valve of the present invention.

FIG. 3A is a longitudinal cross-sectional view of the catheter segment of FIG. 2, showing the low profile valve in the open position.

FIG. 3B is a longitudinal cross-sectional view of the catheter segment of FIG. 2, showing the low profile valve in the closed position.

FIG. 10 is an end view of an alternative embodiment of the inflation adaptor.

FIG. 11 is a cross-sectional view of the inflation adaptor of FIG. 10 along lines 10—10.

FIGS. 18A and 18B are top views of the inflation adaptor of FIGS. 16 and 17, illustrating the latch locking mechanism.

FIGS. 21 and 22 are cross-sectional views of a proximal section of a catheter having an alternative embodiment of the valve of the present invention.

FIG. 23 is a side-elevational view of the balloon-on-a-wire construction incorporating the present invention.

FIG. 24 is a cross-sectional view taken along the line 24—24 of FIG. 23.

FIG. 25 is a cross-sectional view of the proximal removable fitting of the construction shown in FIG. 23.

DETAILED DESCRIPTION OF THE PREFERRED EMBODIMENT

Figure 4:
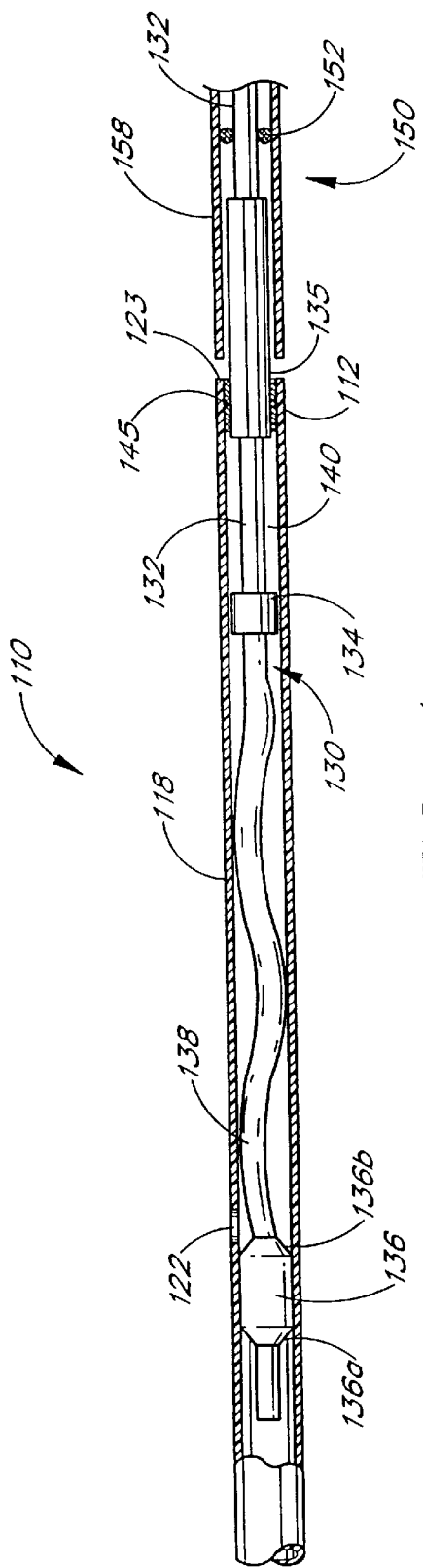
FIG. 4 is a longitudinal cross-sectional view of an alternative embodiment, showing the low profile valve in the closed position.

Referring to FIG. 1, there is depicted a catheter 10 incorporating the low profile valve of the present invention. Although illustrated in the context of a simple occlusion balloon catheter, having a single inflation lumen and a single inflatable balloon, it is to be understood that the low profile valve of the present invention can be readily adapted to a wide variety of balloon catheters, including those having additional functionalities, structures, or intended uses. For example, the low profile valve could be easily adapted to catheters having expandable members other than occlusion balloons, such as therapeutic dilatation balloons. Furthermore, the low profile valve of the present invention may also be incorporated into catheters having two or more lumens. The manner of adapting the low profile valve of the present invention to catheters having these various functionalities, structures, or intended uses will become readily apparent to those of skill in the art in view of the description which follows.

Catheter 10 generally comprises an elongate flexible tubular body 18 extending between a proximal control end 12 and a distal functional end 14. Tubular body 18 has a central lumen 40 which extends between ends 12 and 14. Lumen 40 has an opening 23 at proximal end 12, and is sealed fluid tight at distal end 14. The length of tubular body 18 may be varied considerably depending upon the desired application. For example, where catheter 10 is to be used as a guidewire for other catheters in a conventional percutaneous transluminal coronary angioplasty procedure involving femoral artery access, lengths of tubular body 18 in the range of from about 120 to about 300 centimeters are preferred, with a length of about 180 centimeters often being used. Alternately, for a different treatment procedure, not requiring as long a length of tubular body 18, shorter lengths of tubular body 18 may be provided.

Typically, tubular body 18 will have a generally circular cross-sectional configuration with an outer diameter within the range of from about 0.010 inches to 0.044 inches. Optimally, in most applications where catheter 10 is to be used as a guidewire for other catheters, the outer diameter of tubular body 18 ranges from 0.010 inches to 0.038 inches, and preferably is 0.020 inches in diameter or smaller, more preferably 0.014 inches in outer diameter or smaller. The diameter of lumen 40 will be dictated, in part, by the outside diameter of tubular body 18. For example, where tubular body 18 has an outer diameter of 0.014 inches, central lumen 40 may have an inner diameter of from about 0.008 inches to about 0.010 inches. The diameter of lumen 40 should be large enough to incorporate the low profile valve described below, and large enough to permit sufficient fluid passage for balloon inflation.

Noncircular cross-sectional configurations of lumen 40 can also be adapted for use with the low profile valve of the present invention. For example, triangular rectangular, oval, and other noncircular cross-sectional configurations are also easily incorporated for use with present invention, as will be appreciated by those of skill in the art. The manner of adapting the valve of the present invention will become readily apparent in view of the description which follows.

In the preferred embodiment, the tubular body 18 functions as a guidewire, and thus, tubular body 18 must have sufficient structural integrity, or "pushability," to permit catheter 10 to be advanced through vasculature to distal arterial locations without buckling or undesirable bending of tubular body 18. It is also desirable for tubular body 18 to have the ability to transmit torque, such as in those embodiments where it may be desirable to rotate tubular body 18 after insertion into a patient. A variety of biocompatible materials, known by those of skill in the art to possess these properties and to be suitable for catheter manufacture, may be used to fashion tubular body 18. For example, tubular body 18 may be made of stainless steel, or may be made of polymeric materials such as nylon, polyamide, polyimide, polyethylenes, or combinations thereof. In one preferred embodiment, the desired properties of structural integrity and torque transmission are achieved by forming tubular body 18 out of an alloy of titanium and nickel, commonly referred to as nitinol. In a more preferred embodiment, the nitinol alloy used to form tubular body 18 is comprised of about 50.8% nickel and the balance titanium, which is sold under the trade name Tinel(TM) by Memry Corp. It has been found that a catheter tubular body having this composition of nickel and titanium exhibits great flexibility and improved kink resistance in comparison to other materials. One preferred embodiment of tubular body 18 is disclosed in our copending application entitled HOLLOW MEDICAL WIRES AND METHODS OF CONSTRUCTING SAME, application Ser. No. 08/812,876, filed on Mar. 6, 1997, the entirety of which is incorporated herein by reference.

The distal end 14 of catheter 10 is provided with an atraumatic distal tip 16, and an inflatable balloon 20, as illustrated in FIG. 1. Inflatable balloon 20 may be made from any of a variety of materials known by those of skill in the art to be suitable for balloon manufacture. For example, inflatable balloon 20 may be formed of materials having a compliant expansion profile, such as polyethylene or latex. In one preferred embodiment, where inflatable balloon 20 is to be used as an occlusion balloon, it is preferably formed of a block copolymer of styrene-ethylene-butylene-styrene (SEBS), sold under the trade name C-Flex(TM). One preferred embodiment of a C-Flex occlusion balloon is disclosed in our copending application entitled PRE-STRETCHED CATHETER BALLOON, application Ser. No. 08/812,140, filed on Mar. 6, 1997, the entirety of which is incorporated herein by reference. Alternately, in those embodiments where inflatable balloon 20 is to serve as a dilatation balloon, it may be formed of materials having a noncompliant expansion profile, such as polyethylene terephthalate. Inflatable balloon 20 may be attached to tubular body 18 in any manner known to those of skill in the art, such as heat bonding or through use of adhesives.

As shown in FIG. 1, catheter 10 is provided with a side-access inflation port or opening 22 formed in tubular body 18 at a point several centimeters distal from opening 23. Inflation port 22 is in fluid communication with central lumen 40 extending through tubular body 18. A fill hole (not shown) is formed in tubular body 18 within the region enclosed by inflatable balloon 20, such that fluid passing through inflation port 22 and into lumen 40 may inflate balloon 20. Conversely, an inflated balloon 20 can be deflated by withdrawal of fluid from balloon 20, through lumen 40, and out of side-access inflation port 22.

The low profile valve of the present invention may be used with catheters such as that described above, all well as with different catheters having different structures. In one preferred embodiment, the low profile valve comprises a sealing member which is movably positioned within the inner lumen of a catheter. The catheter has an inflation port, which, in some embodiments, is also an opening to the inner lumen at the proximal end of the catheter. An inflatable balloon is positioned on the distal end of the catheter, which is in fluid communication with the lumen and inflation port. The sealing member is inserted through the proximal opening into the lumen, with a portion of the sealing member extending outwardly from the proximal end of the catheter. The portion of the sealing member inserted into the lumen has a sealer portion which forms a fluid tight seal with the inner lumen to prevent fluid from passing past the sealer portion.

By application of a pushing or pulling force on the extending sealing member portion, the sealing member may be partially advanced within or withdrawn from the lumen, thereby moving the sealer portion within the lumen. In this manner, the sealer portion may be positioned within the lumen either proximally or distally of the inflation port. When the sealer portion is positioned proximally of the port, the valve is in the "open" position. When the valve is open, an unrestricted fluid pathway is established between the inflation port and the balloon, such that an external pressurized fluid source may be connected to the inflation port to inflate the balloon, or if the balloon is already inflated, the balloon may be deflated by application of a vacuum to the inflation port to withdraw fluid from the balloon. When the sealer portion is positioned distally of the inflation port, the valve is in the closed position, as the fluid tight seal between the lumen and the sealer portion prevents fluid from passing either to or from the balloon through the inflation port. Furthermore, when the valve is closed after balloon inflation, the fluid tight seal created by the sealer portion maintains the balloon in the inflated state in the absence of an external fluid source, by preventing the pressurized fluid within the balloon from escaping.

Referring to FIGS. 2, 3A and 3B, there is depicted one embodiment of the low profile valve of the present invention, as used with the catheter of FIG. 1. Catheter 10, as described above, has a side-access inflation port 22 which is in fluid communication with central lumen 40, and through which fluid may be introduced to inflate balloon 20. Central lumen 40 has an opening 23 at proximal end 12. A sealing member 30 is inserted into lumen 40 through opening 23. Sealing member 30 may be partially advanced within or withdrawn from lumen 40 by the application of a longitudinal force on sealing member 30 directed toward or away from proximal end 12, respectively.

Sealing member 30 comprises a main shaft 33, a tapering region 31, and a wire 32. Sealing member 30 may be formed as solid piece out of suitable metals, such as stainless steel, nitinol and the like. For example, sealing member 30 may be formed as a solid cylindrical piece, and then be coined down at points along its length to form tapering region 31 and wire 32. Alternately, one or more of the main shaft 33, tapering region 31, or wire 32 may be formed separately, and then attached to the other piece(s) by conventional means, such as soldering, to form sealing member 30. Polymeric materials, such as Delron™, nylon, and the like, may also be used to form sealing member 30, either as a solid piece, or as separate pieces which are later joined to form the sealing member.

Although not required, in one preferred embodiment, main shaft 33 has an outer diameter no larger than the outer diameter of the catheter tubular body 18. Thus, if the outer diameter of tubular body 18 is 0.014 inches, the diameter of main shaft 33, and thus the largest diameter of sealing member 30, is no larger than 0.014 inches. Furthermore, it is also preferred that main shaft 33 extend proximally from opening 23 by a distance of at least several centimeters to facilitate the application of longitudinal forces on main shaft 33 to manipulate the position of wire 32 in lumen 40. Moreover, after catheter 10 has been fully inserted into a patient, an extending main shaft 33 advantageously functions much like a conventional guidewire extension, providing a starting point for the clinician to insert other catheters over main shaft 33 and catheter 10.

The combined length of catheter 10 and extending main shaft 33 may be varied considerably at the point of manufacture, and may be adapted to the requirements of the other catheters which are to be used with catheter 10 and main shaft 33. For example, where catheter 10 is to be used as a guidewire for other catheters in an "over-the-wire" embodiment, it is preferred that the total length of catheter 10 with extending main shaft 33 be about 300 centimeters. Alternately, when catheter 10 is to be used as a guidewire for other catheters in a single operator embodiment, or "RAPID-EXCHANGE" embodiment, it is preferred that the total length of catheter 10 with extending main shaft 33 be about 180 centimeters. As can be readily appreciated, the individual lengths of catheter 10 and extending main shaft 33 can be varied considerably and yet still achieve the overall desired combined length. For example, a catheter 10 having a length of 180 centimeters can be provided with an extending main shaft 33 having a length of 120 centimeters, to achieve the 300 centimeter total desired length for over-the-wire embodiments.

In another embodiment, where it is undesirable to have a long main shaft extending proximally from catheter 10, a main shaft extending proximally only several centimeters may be provided. The shorter main shaft may be provided with an attachment (not shown), which is adapted to releasably secure longer extensions to the main shaft, such that it can also be used to facilitate the use of catheter 10 as a guidewire for other catheters.

It is preferred that main shaft 33 have a larger diameter than the other portions of sealing member 30, to make it easier to apply moving forces to sealing member 30. Thus, a tapering region 31 may be disposed between main shaft 33 and wire 32, to transition the outer diameter of sealing member 30 from the larger diameter of main shaft 33 to the smaller diameter of wire 32. For the embodiment illustrated in FIGS. 1–3, it is wire 32 which is slidably inserted through opening 23 and into lumen 40. Accordingly, the outer diameter of wire 32 must be less than the inner diameter of lumen 40, so that wire 32 may be slidably accommodated therein. Moreover, in those embodiments where the end of wire 32 extends distally past inflation port 22 when the valve is in the open position, the gap between the outer diameter of wire 32 and the inner diameter of lumen 40 must be sufficiently large so as not to significantly restrict the flow of fluid passing through lumen 40 to or from inflation port 22. Optimally, to facilitate the sliding of wire 32 within lumen 40 and to permit inflation fluid flow, wire 32 is from about 0.001 inches to about 0.004 inches smaller in outer diameter than the inner diameter of lumen 40.

In a preferred embodiment, wire 32 and catheter 10 are provided with positive stops to prevent the withdrawal of wire 32 from the proximal end of catheter 10. For the embodiment depicted in FIGS. 3A and 3B, this consists of a pair of cooperating annular rings mounted on wire 32 and lumen 40, respectively. A first annular ring 34 is coaxially and fixedly mounted on wire 32 at a point on wire 32 contained within lumen 40. A second corresponding fixed annular ring 35 projects inwardly from the interior surface of lumen 40 near proximal end 12. The inner diameter of the opening of annular lumen ring 35 is slightly larger than the outer diameter of wire 32, so as not to restrict the movement of wire 32 within lumen 40. However, the outer diameter of annular wire ring 34 is greater than the inner diameter of the opening of ring 35, such that rings 34 and 35 cooperate to prevent wire 32 from being withdrawn from the proximal end of catheter 10.

Rings 34 and 35 may be formed of any material which may be attached to wire 32 and lumen 40, respectively, and which possesses sufficient structural rigidity to act as a stop. Examples of suitable materials are metals and various hard polymers, such as stainless steel and Teflon(TM). In one preferred embodiment, where wire 32 and tubular body 18 are both formed of nitinol, rings 34 and 35 are also formed of nitinol and are soldered to wire 32 and the inner surface of lumen 40, respectively.

As will be appreciated by those of skill in the art, cooperating stopping structures other than those described herein may also be used to prevent full withdrawal of wire 32 from catheter 10. For example, annular ring 34 may be replaced by one or more protrusions extending radially outwardly from wire 32, which are also adapted to cooperate with ring 35 to prevent withdrawal of wire 32. Alternately, annular ring 35 might be replaced by crimping tubular body 18 slightly to restrict movement of ring 34 to points proximal of the crimp.

A lumen sealer portion 36 is coaxially and fixedly mounted on wire 32. Sealer portion 36 is positioned on wire 32 at a point distal to ring 34, such that by partial withdrawal of wire 32 from catheter 10, as depicted in FIG. 3A, sealer portion 36 is capable of being positioned within lumen 40 at a point proximal to inflation port 22. Sealer portion 36 is also located on wire 32 at a point such that when wire 32 is fully inserted into lumen 40, as depicted in FIG. 3B, sealer portion 36 either fully covers inflation port 22, or is located within lumen 40 at a point distal to inflation port 22. The leading edge 36a and trailing edge 36b of sealer portion 36 are preferably tapered, so that the edges of sealer portion 36 do not catch upon inflation port 22 when sealer portion 36 passes by port 22.

It is preferred that sealer portion 36 form a fluid tight seal with the outer diameter of wire 32 and the inner diameter of lumen 40, such that fluid in lumen 40 is prevented from flowing past sealer portion 36. In the embodiment illustrated in FIGS. 3A and 3B, this is achieved by providing wire 32 with a sealer portion 36 that firmly contacts the entire inner circumference of a section of lumen 40 along a substantial portion of the length of sealer portion 36. The fit between the outer surface of sealer portion 36 and the inner surface of lumen 40 is tight, such that a fluid tight seal is created which prevents fluid from passing past sealer portion 36. However, sealer portion 36 must be capable of being moved within lumen 40 upon movement of main shaft 33, tapering region 31, and wire 32. Thus, the fit between sealer portion 36 and lumen 40 must not be so tight as to prevent movement of sealer portion 36 in lumen 40 upon application of sufficient longitudinal force on main shaft 33. Moreover, the fluid tight seal created by the fit between lumen 40 and sealer portion 36 must be maintained as sealer portion 36 is moved back and forth within lumen 40.

Sealer portion 36 must also be capable of maintaining a seal at fluid pressures conventionally used to inflate catheter balloons, and should be capable of maintaining a seal at pressures which exceed conventional inflation pressures. Preferably, sealer portion 36 is capable of maintaining a seal at pressures up to about 10 atmospheres, more preferably pressures up to about 30 atmospheres, and most preferably at pressures up to about 60 atmospheres. Sealer portion 36 is also preferably capable of undergoing multiple valve-opening and valve-closing cycles without losing the structural integrity required to form seals capable of withstanding pressures of from about 10 atmospheres to about 60 atmospheres. Optimally, sealer portion 36 is capable of undergoing at least 10, and preferably at least 20, valve-opening and closing events and still be capable of maintaining a fluid tight seal at a pressure of 10 atmospheres.

In one embodiment, the desired properties of sealer portion 36 are attained by forming sealer portion 36 out of an extruded polymeric tubing. Pebax(TM) tubing having an inner diameter of 0.008 inches and an outer diameter of 0.017 inches, and a hardness of 40 durometers, is first necked by heating the extruded tubing to a temperature of between 210 and 250 degrees Fahrenheit. Tube pieces of about 0.5 mm in length are then cut from the larger tubing. The cut Pebax(TM) tubes are then placed on a nitinol wire having an outer diameter of about 0.006 inches, and are heated and shaped to recover a tube that has an outer diameter of between 0.010–0.011 inches. The adhesive Loctite 4014(TM) may then be used to bond the heat-shaped Pebax(TM) tubing to the nitinol wire. When the adhesive dries, the leading and trailing edges of the bound Pebax(TM) seal may be trimmed, leaving an annular lumen contact length of about 0.010 inches (0.25 mm). The wire bearing the Pebax(TM) sealer portion may then be inserted into the opening of a nitinol catheter having a lumen with an inner diameter of about 0.0096 inches. Sealer portions of this type have been observed to hold pressures of up to 30 atmospheres, and are capable of undergoing multiple valve-opening and closing events without significantly diminishing the seal strength.

As will be appreciated by those of skill in the art, different forms of Pebax(TM) staring materials may be used to form sealer portion 36. For example, in another preferred embodiment, similar steps were used with a Pebax(TM) tube having similar dimensions but a hardness of 70 durometers, to create a sealer portion.

It is contemplated by the present inventors that methods and materials other than those described above may be used to make a lumen sealer portion having the desired properties. For example, materials other than Pebax(TM), silicone, latex rubber, C-Flex(TM), Nusil(TM) and gels, which are known to possess adequate surface properties to function as a sealer portion, and also be lubricous enough to be moved within lumen 40, may also be used to form sealer portion 36. In addition, sealer portion 36 may be attached to wire 32 by alternate means, such as by integrally molding sealer portion 36 to wire 32, dip forming sealer portion 36 to wire 32, as well as other means of attaching a polymeric material to a wire known to those of skill in the art.

Other embodiments of sealer portion may not create a completely fluid tight seal between the sealer portion and the inner lumen at balloon inflation pressures. In these embodiments, however, the sealer portion creates a seal which prevents substantially all inflation fluid flow past the sealer portion, such that the inflatable occlusive device is maintained in an almost fully expanded state for extended periods of at least one minute, preferably 2 or more minutes, more preferably at least 10 minutes, and optimally at least 20 minutes or longer, and still be capable of providing clinically effective occlusion of any emboli particles in the blood vessel during this time period.

In a preferred embodiment, there is provided movement-force increasing structure, to increase the force required to move sealer portion 36 from the valve-closed to the valve-open position. Structure of this type advantageously minimizes the risk of an accidental opening of the valve, and subsequent balloon deflation, during a medical procedure. In the embodiment illustrated in FIGS. 3A and 3B, this is achieved by providing a biasing spring 37, which surrounds wire 32 between stops 34 and 35. Spring 37 exerts a force on stop 34, pushing it, and thus wire 32 and sealer portion 36, in the distal direction, so that sealer portion 36 forms a fluid tight seal by either covering port 22 or by being positioned within the lumen at a point distal to port 22. Consequently, in the absence of a competing force, spring 37 maintains sealer portion 36 in the valve-closed position. Sealer portion 36 may be moved proximally to the valve-open position by application of a longitudinal force on main shaft 33 directed proximally from end 12 of sufficient magnitude to overcome the force of spring 37. Optimally, spring 37 is selected so that the force that must be applied to main shaft 33 to overcome the force of spring 37 is from about 0.3 to about 1.0 pound-foot. In alternative embodiments, the movement force increasing structure may comprise waves introduced into the wire just proximal of the sealer portion, as described below, which also may require 0.3 to 1.0 pound-foot of force to overcome.

Figure 5:
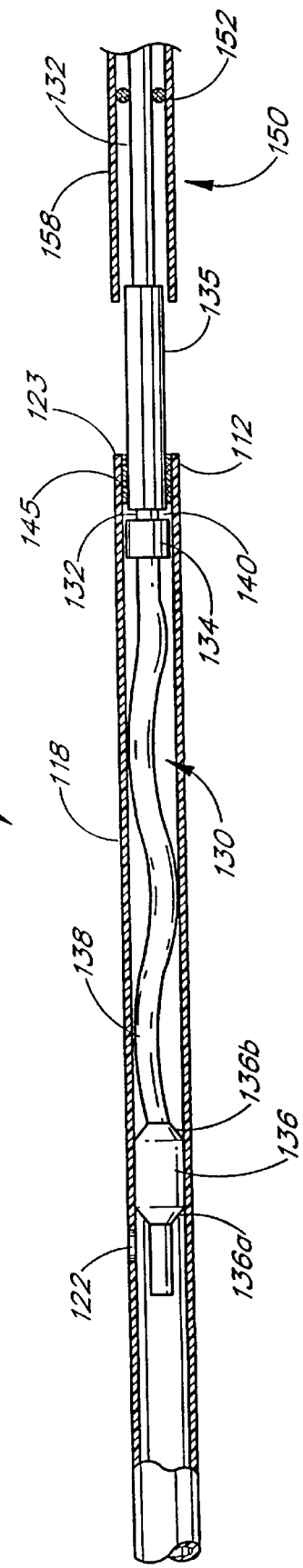
FIG. 5 is a longitudinal cross-sectional view of the embodiment of FIG. 4, showing the low profile valve in the open position.

Referring to FIGS. 4 and 5, there is illustrated in alternative embodiment of the valve of the present invention. The alternative embodiment comprises a catheter 110 which may have features which are substantially identical, in materials, structure, and function, as the catheter described in connection with FIGS. 1–3. Catheter 110 has a proximal end 112, and a distal end (not shown) to which is mounted an expandable member, such as an inflatable balloon. A central lumen 140 extends within tubular body 118 between the proximal and distal ends. An opening 123 to lumen 140 is present at the proximal end 112 of catheter 110.

A sealing member 130 is inserted into lumen 140 through opening 123, as described previously. Sealing member 130 comprises a sealer portion 136, a wire 132, annular rings 134 and 135, and support member 150. Sealing member 130 may be formed out of materials and by methods as described previously.

As illustrated in FIGS. 4 and 5, the outer diameter of wire 132 is less than the inner diameter of lumen 140, such that sealing member 130 is slidably insertable into lumen 140. Furthermore, a lumen sealer portion 136 is coaxially and fixedly mounted to wire 132 near the distal end of wire 132. Sealer portion 136 forms a fluid tight seal with the outer diameter of wire 132 and the inner diameter of lumen 140, such that fluid introduced into lumen 140 through opening 122 is prevented from flowing past sealer portion 136 at normal balloon inflation pressures of 1 to 3 atmospheres for occlusive devices, and as much at 10 atmospheres or more for other types of balloons. Sealer portion 136 may be provided with leading edge 136a and trailing edge 136b, both tapered, to facilitate movement of sealing portion 136 proximally and distally of inflation port 122. Sealer portion 136 forms a fluid tight seal by filling contacting the entire inner circumference of a section of lumen 140 along a substantial portion of the length of sealer portion 136. As described previously, sealer portion 136 prevents substantially all fluid flow past the seal created by sealer portion 136, and the movement of sealer portion 136 proximally and distally of port 122 may be used to effect the valve-open and valve-closed positions.

Cooperating positive stops, consisting of hollow cylinders 134 and 135 are provided to prevent withdrawal of sealing member 130 from lumen 140. Hollow cylinder 135 is attached to the inner surface of lumen 140 by adhesives, soldering, crimping, or by other means known to those of skill in the art, such that the proximal portion of hollow cylinder 135 extends within lumen 140, and is secured therein, and the distal portion of cylinder 135 extends from proximal end 112. Cylinder 135 has a lumen (not shown) extending therethrough. The diameter of the cylinder lumen is larger than the outer diameter of wire 132, so that movement of wire 132 is not restricted. A second hollow cylinder 134, preferably of shorter length, is placed over wire 132 and is fixedly mounted to wire 132, by soldering, or other means, at a point distal to cylinder 135. The outer diameter of cylinder 134 is less than the inner diameter of lumen 140, so as not to restrict the movement of wire 132 within lumen 140. However, the outer diameter of cylinder 134 is greater than the inner lumen diameter of cylinder 135, so that cylinders 134 and 135 act as cooperating stops, to prevent wire 132 from being withdrawn from lumen 140. Cylinders 134 and 135 may be formed of any material which may be attached to wire 132 and lumen 140, respectively, and which possesses sufficient structural rigidity to act as a stop. Examples of suitable materials are metals and various hard polymers, such as stainless steel, Teflon(TM), and the like. In one preferred embodiment, where wire 132 and tubular body 118 are both formed of nitinol, cylinders 134 and 135 are also formed of nitinol, and are soldered to wire 132 and the inner surface of lumen 140, respectively.

The distal portion of cylinder 135 extending from proximal end 112 is inserted into support member 150. Support member 150 comprises a tubular body 158 having an outer diameter and inner lumen diameter which are approximately the same as tubular body 118. Consequently, because the outer diameter of cylinder 135 is less than the inner lumen diameter of support member 150, the extending portion of cylinder 135 is slidably disposed within the support member 150 inner lumen.

Wire 132 extends proximally from cylinder 135 within support member 150, as shown in FIGS. 4 and 5. A segment of wire 132 within support member 150 is secured to support member 150 at point 152. Wire 132 may be secured to support member 150 by any means known to those of skill in the art, including use of adhesives, crimping, soldering or welding. Because wire 132 is secured to support member 150, the application of longitudinal forces on support member 150 results in movement of sealing member 130 within lumen 140, to open or close the valve of the present invention, as described above with respect to FIGS. 1–3. Advantageously, use of support member 150 protects wire 132 from undesirable kinking or bending when sealing member 130 is moved.

As illustrated in FIGS. 4 and 5, sealing member 130 has movement-force increasing structure which increases the force required to move sealing member 130 within lumen 140. The movement-force increasing structure consists of waves 138 formed in wire 132 just proximal to sealer portion 136. Waves 138 contact the inner surface of lumen 140, thereby increasing the frictional forces which must be overcome to move wire 132 within lumen 140. In one preferred embodiment, where wire 132 is made of nitinol and has an outer diameter of 0.006 inches, and is inserted into a nitinol catheter which has an inner lumen 140 with the diameter of about 0.010 inches, waves are formed on wire 132 for one and one-half cycles with an amplitude of about 0.016 inches to increase the valve-opening movement force.

Figure 6:
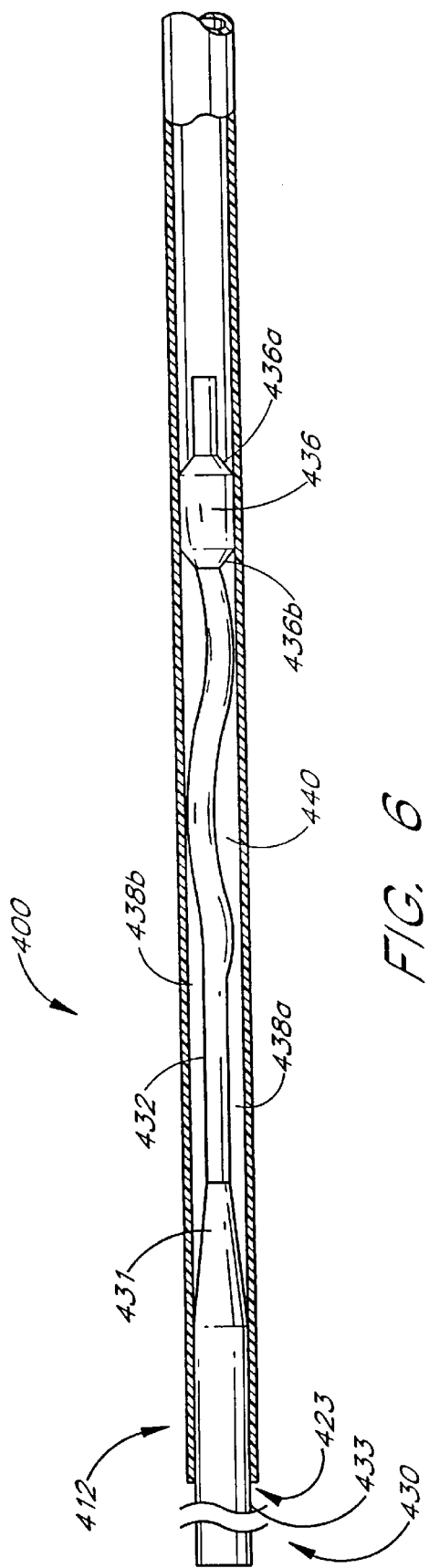
FIG. 6 is a longitudinal cross-sectional view of an alternative embodiment of the low profile valve, depicting the valve in the open position
Figure 7:
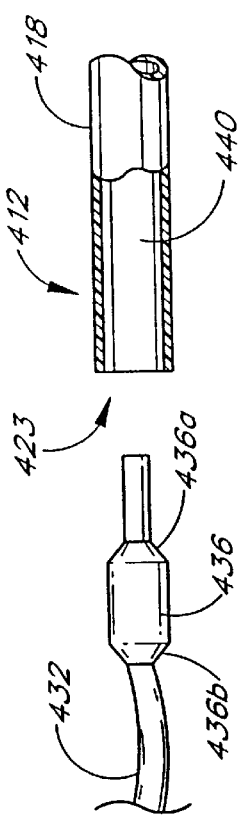
FIG. 7 is a longitudinal cross-sectional view of the embodiment of FIG. 6, depicting the valve in the closed position.

Referring to FIGS. 6 and 7, there is illustrated another embodiment of the present invention. Referring to FIG. 6, there is provided a catheter 400 having a tubular body 418 and inflatable balloon (not shown) as described above. Catheter 400 may be formed of materials and methods as described above, and may have structural aspects identical to those described previously, except where otherwise noted. In particular, as shown in FIGS. 6 and 7, catheter 400 is not provided with a side-access port on the catheter tubular body, nor is there provided cooperating positive stops on the wire and lumen. Instead, the sealer portion may be fully withdrawn from the lumen. Once the sealer portion is removed, the proximal opening serves as an access port for attached devices to inflate or deflate the balloon. The sealer portion can be inserted through the proximal opening into the lumen after balloon inflation to maintain the balloon in the inflated state.

Catheter 400 has a proximal end 412, and a distal end (not shown) to which is mounted an inflatable balloon. A central lumen 440 extends within tubular body 418 between the proximal and distal ends. An opening 423 to lumen 440 is present at the proximal end 412 of catheter 400.

A sealing member 430 is inserted into lumen 440 through opening 423. Sealing member 430 has a main shaft 433, a tapering region 431, and a wire 432. Sealing member 430 may be formed of materials and by methods as described previously. As illustrated in FIGS. 6 and 7, the outer diameter of main shaft 433 is less than the inner diameter of lumen 440, such that main shaft 433 is slidably insertable into lumen 440. In addition, the outer diameters of tapering region 431 and wire 432 are also smaller than main shaft 433, and thus lumen 440, such that tapering region 431 and wire 432 are also slidably insertable in lumen 440. A portion of main shaft 433 preferably extends proximally from end 412, to facilitate application of moving forces upon sealing member 430 to move wire 432 within lumen 440, as described previously.

As illustrated in FIGS. 6 and 7, sealing member 430 has movement-force increasing structure which increases the force required to move sealing member 430 within lumen 440. The movement-force increasing structure consists of waves 438a and 438b formed in wire 432 near its distal end. Waves 438a and 438b contact the inner surface of lumen 440, thereby increasing the frictional force which must be overcome to move wire 432 within lumen 440. In one preferred embodiment, where wire 432 is made of nitinol and has an outer diameter of 0.006 inches, and is inserted into a nitinol catheter which has an inner lumen 440 with a diameter of about 0.010 inches, waves are formed on wire 432 for 1½ cycles with an amplitude of about 0.016 inches to increase the valve-opening movement force.

A lumen sealer portion 436 is coaxially and fixedly mounted on wire 432. Sealer portion 436 forms a fluid tight seal with the outer diameter of wire 432 and the inner diameter of lumen 440, such that fluid introduced into lumen 440 through opening 423 is prevented from flowing past sealer portion 436 when sealer portion 436 is inserted into lumen 440. Sealer portion 436 forms the fluid tight seal by firmly contacting the entire inner circumference of a section of lumen 440 along a substantial portion of the length of sealer portion 436, and may be formed of materials and by methods as previously described.

In some removable sealing member embodiments, the sealing member is not provided with a separate sealing portion, as described above. In these embodiments, the sealing member itself functions as a sealing portion which is inserted into the proximal opening to restrict fluid flow, and which may be partially or wholly removed to provide for a fluid pathway between the proximal opening and an expandable member on the distal end of the catheter. Preferably, the sealing members of these embodiments comprise a tapering rod, which at its distal end, has an outer diameter smaller than the inner lumen diameter of the catheter in which it is inserted as a plug, such that the distal end of the rod may be easily inserted into the catheter lumen through the proximal opening. The tapering rod increases in outside diameter at points proximal to the distal end. Consequently, one or more points of the rod have an outside diameter greater than the inner lumen diameter of the catheter in which it is inserted as a plug, such that by forcing the rod into proximal opening, the larger outer diameter of the rod forms a relatively fluid tight seal with the catheter lumen at the proximal opening of the catheter. An O-ring, or other polymeric structure, may be mounted in the inner lumen of the catheter at or near the proximal opening, to cooperate with the tapering rod in the creation of the seal. Thus, in this embodiment, the point where the seal is created does not move with respect to the catheter, but is instead stationary at or near the proximal opening of the catheter.

Figure 12:
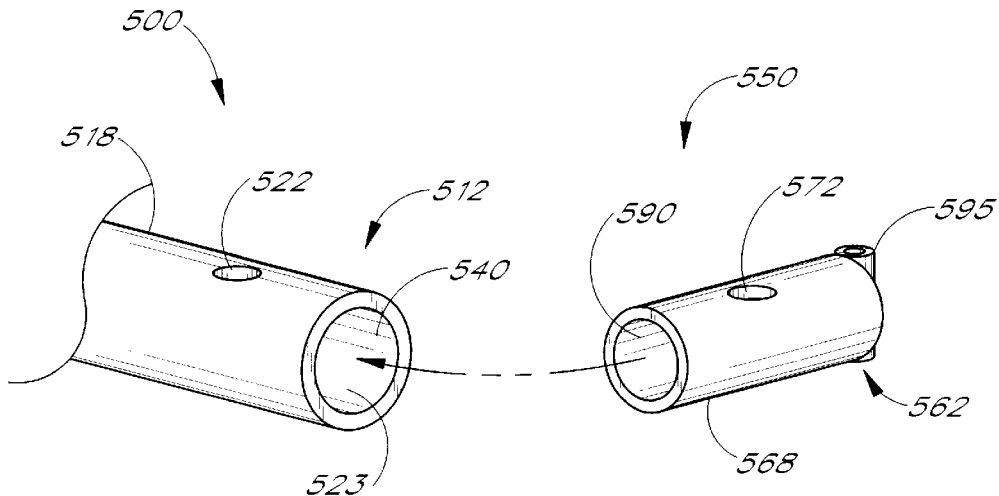
FIGS. 12 and 13 are exploded views of alternative embodiments of the low profile valve of the present invention.

Referring to FIG. 12, there is depicted an alternative embodiment of the valve the present invention. The alternative embodiment is provided to a catheter 500, formed of a tubular body 518 and having a proximal end 512. Catheter 500 has an opening 523 at is proximal end, and a lumen 540 extending the length of the tubular body. Lumen 540 is in fluid communication with an expandable member (not shown) mounted on the distal end of tubular body 518. A side-access port 522 is provided in tubular body 518 at a point distal to proximal end 512. Catheter 500 may have aspects identical, both in structure, dimensions, materials, and construction, to catheters described previously.

A sealing member 550 is positioned within lumen 540 near proximal opening 523 and side-access port 522. Sealing member 550 is formed from a short tubular body 568, having a lumen 590, which is sealed at end 562, but open at the other end. Sealing member 550 has an outer diameter slightly larger that the inner diameter of lumen 540, but smaller than the outer diameter of tubular body 518, such that sealing member 550 may be tightly fit within lumen 540 through opening 523, to form a fluid tight seal over catheter proximal opening 523. Cooperating stopping structures (not shown) may be provided to sealing member 550 and catheter 500 to prevent removal of sealing member 550 from lumen 540 at elevated pressures. Sealing member 550 may be formed out of the same materials as tubular body 518.

Tubular body 568 is provided with an opening 572 extending therethrough. Opening 572 is positioned on tubular body 568 such that opening 572 is capable of aligning with side-access port 522 when sealing member 550 is rotated within lumen 540, or is moved proximally or distally within lumen 540. A rotation element 595, such as a perpendicular attachment, may be provided facilitate rotation of sealing member 550 within lumen 540. Other rotation elements, such as notches or grooves, may be used in place of the perpendicular attachment, as will be appreciated by those of skill in the art.

Sealing member 550 functions as a valve within catheter 500, controlling fluid flow through side-access port 522. When sealing member 550 is rotated so that port 522 and opening 572 are aligned, fluid may flow through port 522 through lumen 540 to inflate the occlusive device. Upon the desired inflation, sealing member 550 may be rotated, as for example by ninety degrees, or moved proximally or distally within lumen 540, such that opening 572 is no longer aligned with port 522, and tubular body 568 blocks fluid flow through port 522.

Figure 13:
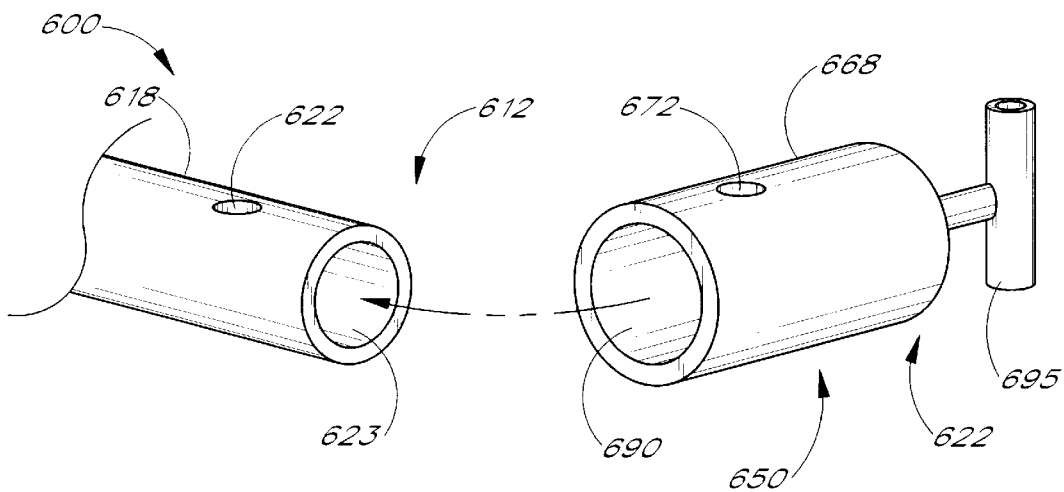

Shown in FIG. 13, is an alternative embodiment of the rotatable sealing member. Numerals corresponding to those of the embodiment of FIG. 12 have been used to illustrate the similar structural aspects between the two embodiments. Sealing member 600 is identical in construction to the sealing member of FIG. 12, except that sealing member 650 is somewhat larger, and is adapted to be slipped over tubular body 618. The respective diameters of tubular body 618 and sealing member lumen 690 are such that a fluid tight seal is created over lumen 623. Side-access inflation port 622 may be aligned with opening 672, as above, by rotation or longitudinal movement, to provide fluid access to lumen 640 through port 622.

In certain embodiments, it may be desirable for sealing members 550 and 650 to have a longer length, such that they may function as an extension for other catheters to be inserted over catheters 500 and 600. In these embodiments, sealing members 550 and 650 may be formed with longer tubular bodies, or be provided with attachments so that extension members may be releasably secured thereto.

Figure 14:
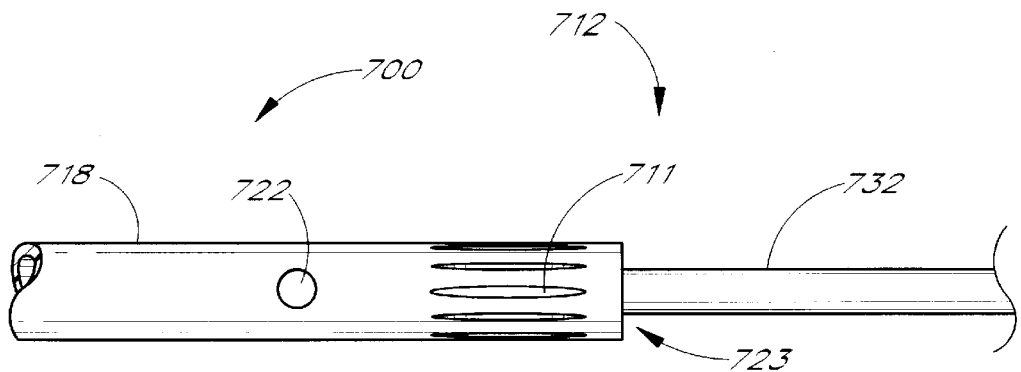
FIG. 14 is an alternative embodiment of the valve of the present invention featuring a built in spring bias.
Figure 15A:
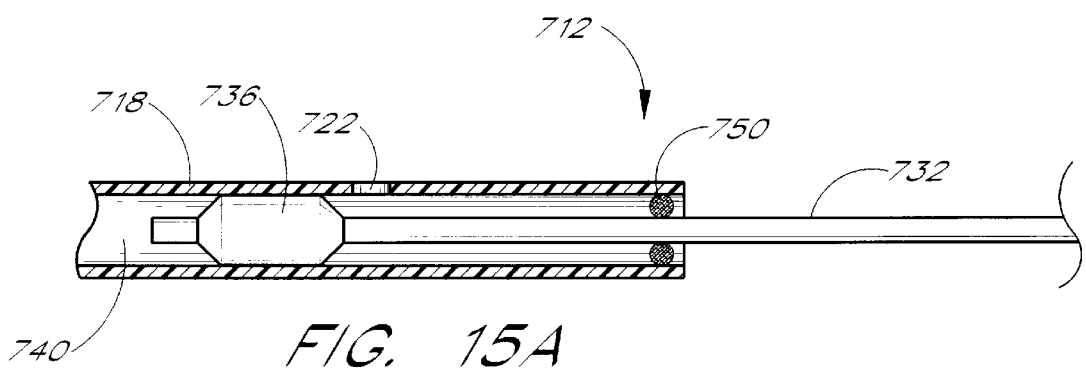
FIGS. 15A and 15B are longitudinal cross-sectional views of the catheter proximal end of FIG. 14, showing the valve in the closed and open position, respectively.
Figure 15B:
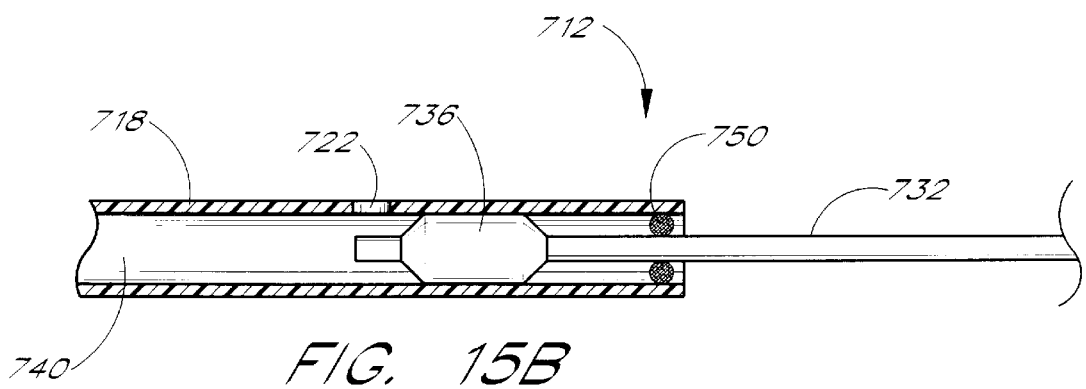

Referring to FIGS. 14, 15A and 15B, there is illustrated an alternative embodiment of the present invention featuring a self-closing valve. The alternative embodiment comprises a catheter 700 having an elongate flexible tubular body 718 extending between a proximal control end 712 and a distal functional end (not shown), and having a balloon (not shown) as described previously. Tubular body 718 has central lumen 740 which extends between the proximal and distal ends. Lumen 740 has an opening 723 at proximal end 712, and is sealed fluid tight at the distal end. A side access inflation port 722 is formed in tubular body 718 at a point distal of opening 723. Inflation port 722 and lumen 740 are in fluid communication with the distal inflatable balloon, as described previously.

A wire 732 is inserted into opening 723, and is slidably disposed within lumen 740. Accordingly, the outer diameter of the wire 732 must be less than the inner diameter of lumen 740, so that wire 732 may be slidably accommodated therein. A sealer portion 736 is coaxially mounted on wire 732. Sealer portion 736 is of similar type and construction to the sealer portion described in connection with FIGS. 1–3. Sealer portion 736 is positioned on wire 732 at a point distal to inflation port 722, and forms fluid-tight seal with the outer diameter of wire 732 and the inner diameter of lumen 740, such that fluid introduced into lumen 740 is prevented from flowing past sealer portion 736. Consequently, because sealer portion 736 is positioned with lumen 740 distal to inflation port 722, sealer portion 736 is in the valve-closed position.

In the embodiment depicted in FIGS. 14–15B, tubular body 718 is formed from a material having a certain degree of elasticity, such that if the proximal end 712 of tubular body 718 is secured to wire 732 at point 750, and a longitudinal force is applied to tubular body 718 in a direction distal to end 712, the elasticity of tubular body 718 results in the shifting of inflation port 722 in the distal direction. Moreover, slits 711 may be formed in tubular body 718 near proximal end 712 to enhance the elastic response of tubular body 718, thereby increasing the distal translocation of inflation port 722 upon application of an axial force to tubular body 718. Wire 732 may be secured to tubular body 718 by any means known to those of skill in the art, such as adhesives, welding, soldering, or crimping.

In a preferred embodiment, tubular body 718 is made out of nitinol, and has at least 8% elasticity when longitudinal slits 711 are introduced at the proximal end. As can be observed in FIG. 15A, in the absence of any longitudinal force applied to tubular body 718, sealer portion 736 is positioned within lumen 740 at a point distal to inflation port 722, such that fluid may not pass through port 722 to inflate or deflate the balloon. However, if a longitudinal force is applied to tubular body 718 in the distal direction, and the proximal end of tubular body 718 and wire 732 are held in position, tubular body will stretch, as shown in FIG. 15B, and inflation port 722 will be translocated in the distal direction so that sealer portion 736 will be located within the lumen proximally of port 722. This will establish an unrestricted fluid pathway between inflation port 722 and the distal balloon, so that the balloon may be either inflated or deflated by passage of fluid through port 722. Upon removal of the longitudinal force, the elastic response of tubular body 718 will result in proximal translocation of inflation port 722, and sealer portion 736 will once again be in the valve-closed position.

Figure 8:
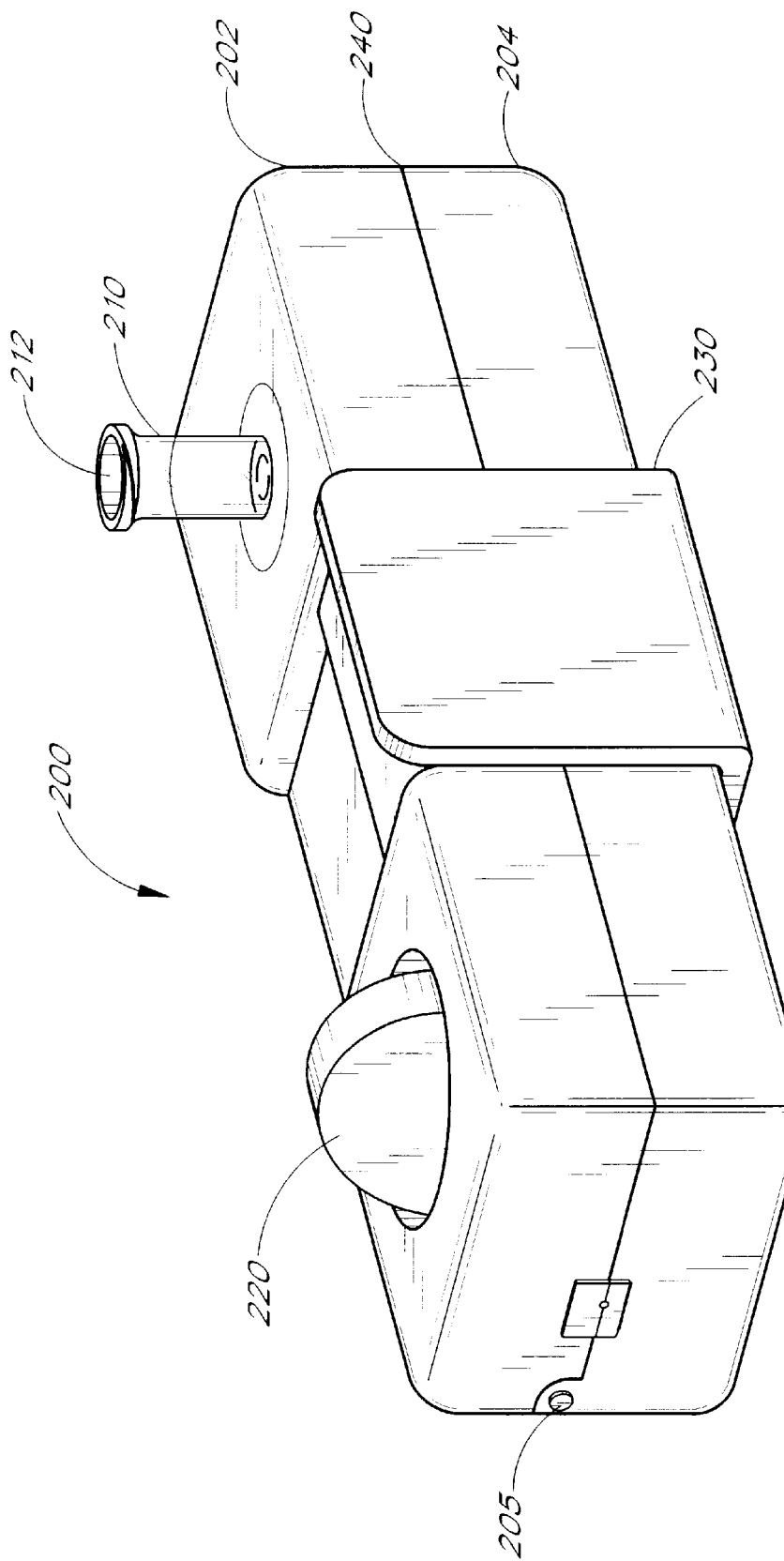
FIG. 8 is a perspective view of an inflation adaptor used to manipulate the low profile valve of the present invention.
Figure 9A:
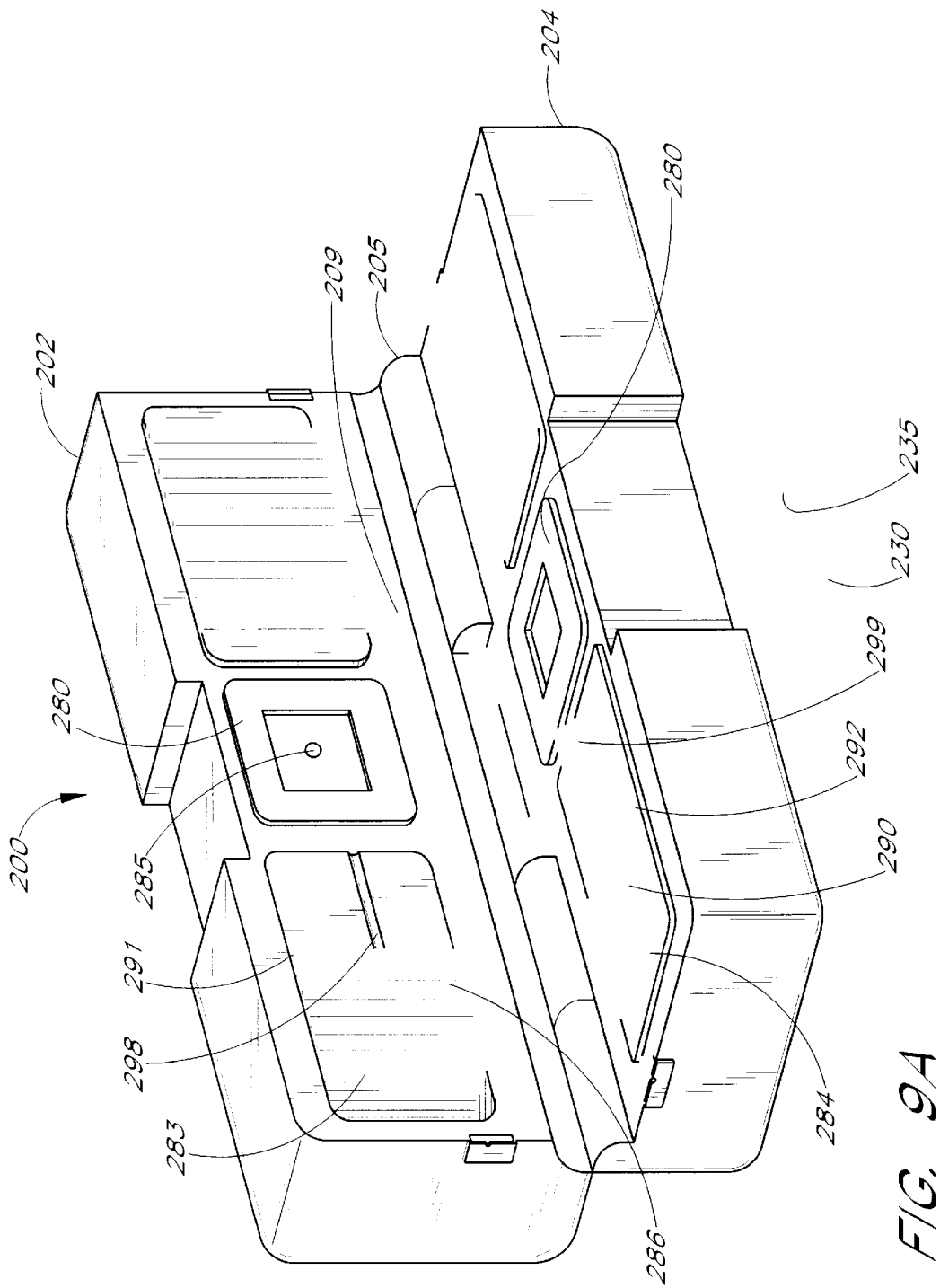
FIG. 9A is a perspective view of the interior of the inflation adaptor of FIG. 8.

Referring to FIGS. 8 and 9A, there is illustrated an inflation adaptor 200 which may be used to inflate and to open and close the low profile valve depicted in FIGS. 1–5. Inflation adaptor 200 comprises a housing having a first half 202 and a second half 204, which are preferably formed of metal, medical grade polycarbonate, or the like. Halves 202 and 204 are attached to one another by a pair of hinges 205 positioned on one of the lateral edges of each half, such that halves 202 and 204 may be separated or joined in a clam shell manner as depicted in FIGS. 8 and 9. A locking clip 230 secures half 202 to half 204 while inflation adaptor 200 is in use. Locking clip 230 may be provided with an angled leading edge 235 to facilitate closing of clip 230 to secure halves 202 and 204 together. Springs 209 may also be provided to facilitate opening of adaptor 200.

A groove 240 separates first half 202 from second half 204 when the halves are closed and clip 230 is secured. Groove 240 is of sufficient width to accept the proximal end of a catheter having the low profile valve of the present invention, as described in detail above. A fitting 210 is positioned on half 202, to create an inflation passageway 212 which terminates in opening 285 on the interior surface of first half 202. Fitting 210 is preferably a standard luer connector which may be attached to a variety of existing external pressurized fluid sources, although other types of fittings, such as tubings, quick connects, and Y-site connections, may be easily substituted for a luer fitting.

A seal comprising a pair of gaskets 280 is positioned around opening 285 on the interior surfaces of halves 202 and 204. Gaskets 280 are in alignment, such that when halves 202 and 204 are brought together and secured by locking clip 230, a fluid tight inflation chamber is created within the interior region defined by gaskets 280. The fluid tight inflation chamber is in fluid communication with fitting 210 via inflation passageway 212, so that a pressurized inflation fluid may be introduced into the fluid tight inflation chamber by attaching an external pressurized fluid source to fitting 210. Moreover, gaskets 280 are preferably formed of resilient materials, such as silicone, C-Flex(TM) and Pebax (TM), so that gaskets 280 may form-fit over a catheter tubular body which extends across the lateral edges of gaskets 280, to create the fluid tight chamber.

An actuator 220 is positioned on the external surface of half 202. In the embodiment illustrated in FIGS. 8 and 9, actuator 220 controls a cam which operates a sliding panel 283 on the interior surface of half 202. Sliding panel 283 moves back and forth along a line which bisects opening 285. When actuator 220 is moved to a first position, sliding panel 283 moves toward opening 285 along this line. When actuator 220 is moved to a second position, sliding panel 283 moves away from opening 285 along the same line. A corresponding sliding panel 284 is positioned on half 204, such that panels 283 and 284 are aligned and move together when the position of actuator 220 is changed. To facilitate coordinated movement of panels 283 and 284, a pin 286, or such other similar engagement structure, may be provided to releasably secure panel 283 to panel 284 when the adaptor is closed. The length of travel of panels 283 and 284 is preferably adjusted to provide the minimum sufficient distance to position the sealing member in the valve open or valve closed position, as desired.

Panels 283 and 284 each have a roughened surface 290, to facilitate the frictional engagement of panels 283 and 284 with the main shaft portion of the low profile valve. In a preferred embodiment, panels 283 and 284 are both made of silicone, and roughened surface 290 comprises teeth 291 and grooves 292 formed on each of panels 283 and 284. The teeth 291 and grooves 292 cooperate, to permit the teeth of one panel to fit into the grooves of the opposite panel when the adaptor is closed.

For ease of understanding, the operation of inflation adaptor 200 to inflate the balloon of the catheter of FIGS. 1–3 will now be described. Actuator 220 is moved to the first position, so that sliding panels 283 and 284 are moved closer to opening 285. Locking clip 230 is then undone, exposing groove 240. Halves 202 and 204 are then partially separated, and catheter 10, with the balloon 20 deflated, is inserted into the inflation adaptor. As described previously, catheter 10 has an inflation port 22 located near proximal end 12, and a main shaft 33 extending from proximal end 12. Catheter 10, with the low profile valve in the closed position, is placed within groove 240 of partially open adaptor 200, and catheter 10 and main shaft 33 are placed within securing clips 271 and 272, such that when halves 202 and 204 are closed, inflation port 22 will lie within the fluid tight inflation chamber created by gaskets 280, and the extending portion of main shaft 33, but not proximal end 12, will rest between sliding panels 283 and 284. An alignment slot 298 and overlying shelf 299 may be provided to facilitate alignment and prevent buckling or kinking of the catheter and sealing member during use.

Figure 9B:
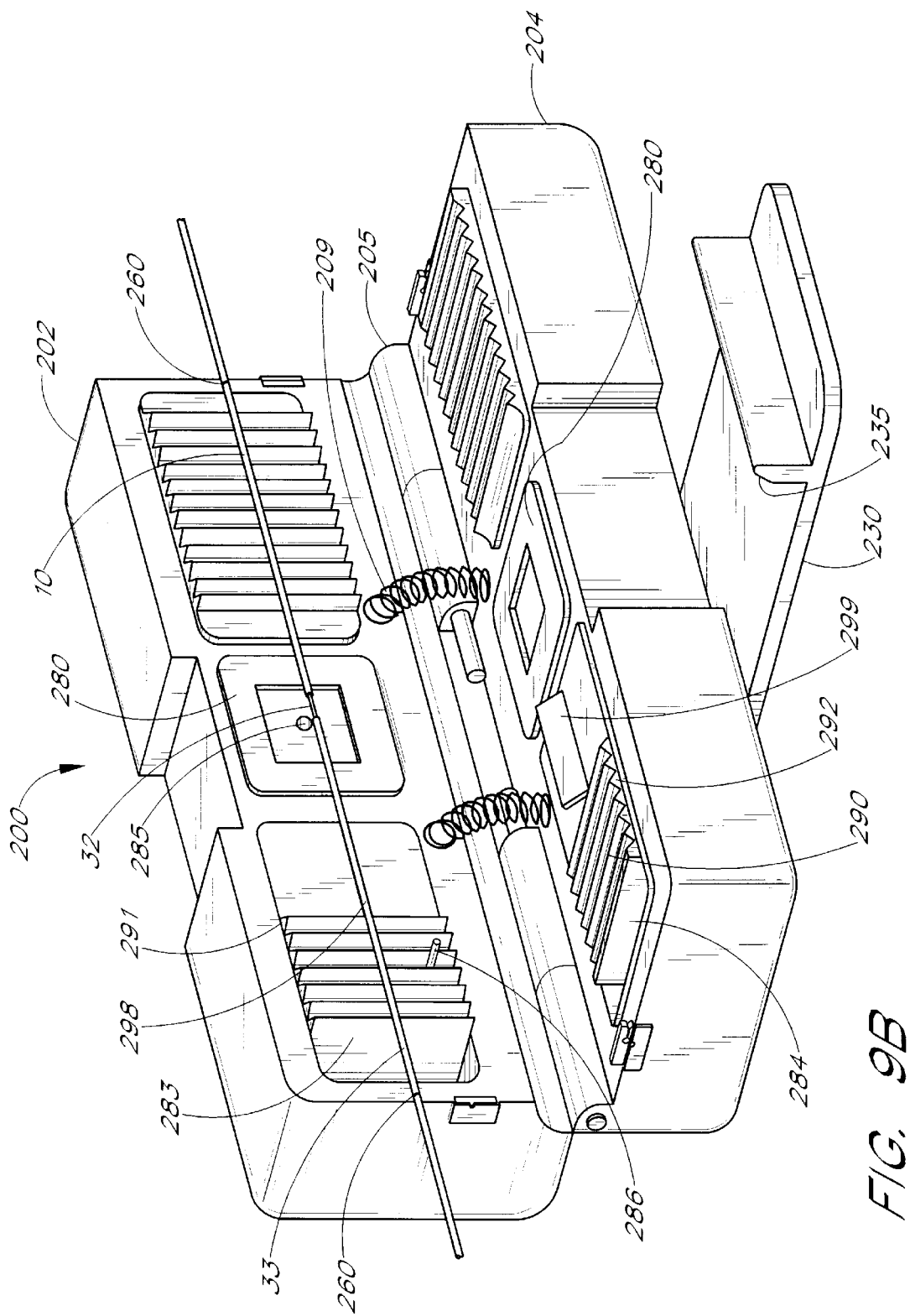
FIG. 9B is a perspective view of a catheter with a sealing member and alignment indicia being positioned in the inflation adaptor of FIG. 9A.

As shown in FIG. 9B, in one embodiment, indicia 260 are provided on catheter 10 and main shaft 33, which when aligned with indicia 270 on inflation adaptor 200, result in alignment of inflation port 22 with the fluid tight inflation chamber of adaptor 200, and alignment of main shaft 33 with sliding panels 283 and 284, when catheter 10 and sealing member 30 are inserted into groove 240. Indicia 260 and 270 may take the form of markings, grooves or notches, or any other suitable means of aligning the valve with the inflation adaptor alignment indicia, may be provided. Preferably, the gap between indicia 260 on catheter 10 and main shaft 33 is approximately equal to the space between clips 271 and 272, such that by placing indicia 260 within clips 271 and 272, catheter 10 and main shaft 33 are properly aligned within adaptor 200.

Indicia solely on the catheter tubular body may also be used to facilitate correct alignment. For example, two visible markings may be place on the catheter on either side of the catheter inflation access port. By inserting the catheter into lower half 204 so that both of these markings are place within lower half gasket 280, the catheter inflation access port will be within the fluid tight inflation chamber created by gaskets 280 when halves 202 and 204 are secured to one another.

Once main shaft 33 and inflation port 22 are properly aligned within adaptor 200, locking clip 230 is secured. Inflation port 22 now lies within the fluid tight inflation chamber created by gaskets 280, and main shaft 33 rests between sliding panels 283 and 284. The clinician may then attach an external pressurized fluid source to fitting 210.

To inflate balloon 20, the clinician moves actuator 220 from the first position to the second position, thereby causing sliding panels 283 and 284 to move away from 30 opening 885. Because main shaft 33 is firmly secured between panels 283 and 284, a longitudinal force directed away from proximal end 12 is applied to main shaft 33. The longitudinal force on main shaft 33 results in wire 32 being partially withdrawn from lumen 40, which causes sealer portion 36 on wire 32 to be moved to a position within lumen 40 which is proximal of inflation port 22. The movement of sealer portion 36 proximally of inflation port 22 opens the low profile valve, by establishing an unrestricted fluid pathway between inflation port 22 and balloon 20.

The external pressurized fluid source may then be activated, as for example by pushing the plunger on a syringe, such that pressurized fluid passes through passageway 212 and opening 285 into the fluid tight inflation chamber. The pressurized fluid then passes through inflation port 22 and lumen 40, to inflate balloon 20.

Inflated balloon 20 may be maintained in the inflated state, in the absence of the pressurized fluid source, by closing the low profile valve. This is accomplished by moving actuator 220 back to the first position, thereby causing sliding panels 283 and 284 to move toward opening 285. The moving panels apply a longitudinal force, directed toward proximal end 12 to main shaft 33, causing wire 32 to be further inserted into lumen 40. Consequently, sealer portion 36 is moved from a position within lumen 40 which is proximal to inflation port 22 to a position in lumen 40 which is distal to inflation port 22. The fluid tight seal created by sealer portion 36 traps the pressurized fluid within lumen 40 and balloon 20, thereby maintaining balloon 20 in the inflated state. The external pressurized fluid source may then be deactivated and removed. Once the low profile valve is closed, inflation adaptor 200 may be removed by unlocking clip 230, and removing catheter 10 and main shaft 33from groove 240.

Referring to FIGS. 10 and 11, there is illustrated an alternative embodiment of an inflation adaptor especially adapted for manipulating removable low profile valves, although it may be used with side-access embodiments as well. Moreover, it should also be appreciated that adaptor 200 and similar type adaptors may also be used to manipulate removable valve embodiments.

Adaptor 300 comprises an outer sleeve 320 formed of metal, medical grade polycarbonate, or similar such materials. Outer sleeve 300 defines a tapering inner lumen 350. Lumen 350 tapers from large diameter 352 which is significantly greater than the outer diameter of the catheter tubular bodies inserted into lumen 350, to a smaller diameter 355, which is slightly larger the outer diameter of the catheter tubular body. Lumen 350 is in fluid communication with an inflation passageway 312 formed by fitting 310, so that a pressurized inflation fluid may be introduced into lumen 350. Releasable seals 315 are positioned at each end of lumen 350, such as to create a fluid tight inflation chamber within lumen 350 when a pressurized fluid source is attached. Releasable seals 350 may comprise any type of seal known to those of skill in the are, such as Toughy Borst connectors, hemostatic valves, and the like. Releasable seals 350 may also act to secure any catheters and sealing members inserted within the releasable seal openings 325.

In use, a catheter and sealing member, such as that described in connection with FIGS. 6–7, is inserted into opening 325 after seals 315 have been opened. The catheter and sealing member are positioned under passageway 312, and the sealing member is removed from the proximal opening of the catheter. A fluid passageway is thereby created between the proximal catheter opening and the expandable member of the distal end of the catheter. Seals 350 are closed to create a fluid tight chamber, and a vacuum and/or pressurized inflation fluid is applied, to inflate or deflate the balloon. After the desired inflation or deflation has occurred, the sealing member may be introduced into the proximal opening of the catheter tubular body to seal the lumen, either by hand or by a movable actuator (not shown). Seals 350 may then be loosened, and the end access adaptor 300 removed by sliding the adaptor off the end of the catheter and sealing member.

Referring to FIGS. 16–18B, there is illustrated an alternative embodiment inflation adaptor 800 which may also be used in conjunction with the low profile valves of the present invention, of the type depicted in FIGS. 1–5, to inflate or deflate catheter balloons. Inflation adaptor 800 comprises a housing having a first half 802 and a second half 804, which are preferably formed of a medical grade polycarbonate. However, as will be appreciated by those of skill in the art, a great many other materials may by used to form adaptor 800, including metals such as 300 series stainless steel and 400 series stainless steel, and polymeric materials such as Acrylonitrile-butadiene-styrene (ABS), Acrylics, and Styrene-acrylonitriles. Furthermore, the individual halves 802 and 804 may be manufactured in a variety of different ways. For example, where polymeric materials are used, it is preferable to use a mold to manufacture each of the halves. Moreover, in some embodiments, more than one molded piece may be used to form an individual half, with the various pieces being joined together by bonding or mechanical means to form a half. Alternately, as is known in the art, the individual halves can be formed through machining processes performed on larger blocks of the raw materials.

Figure 16:
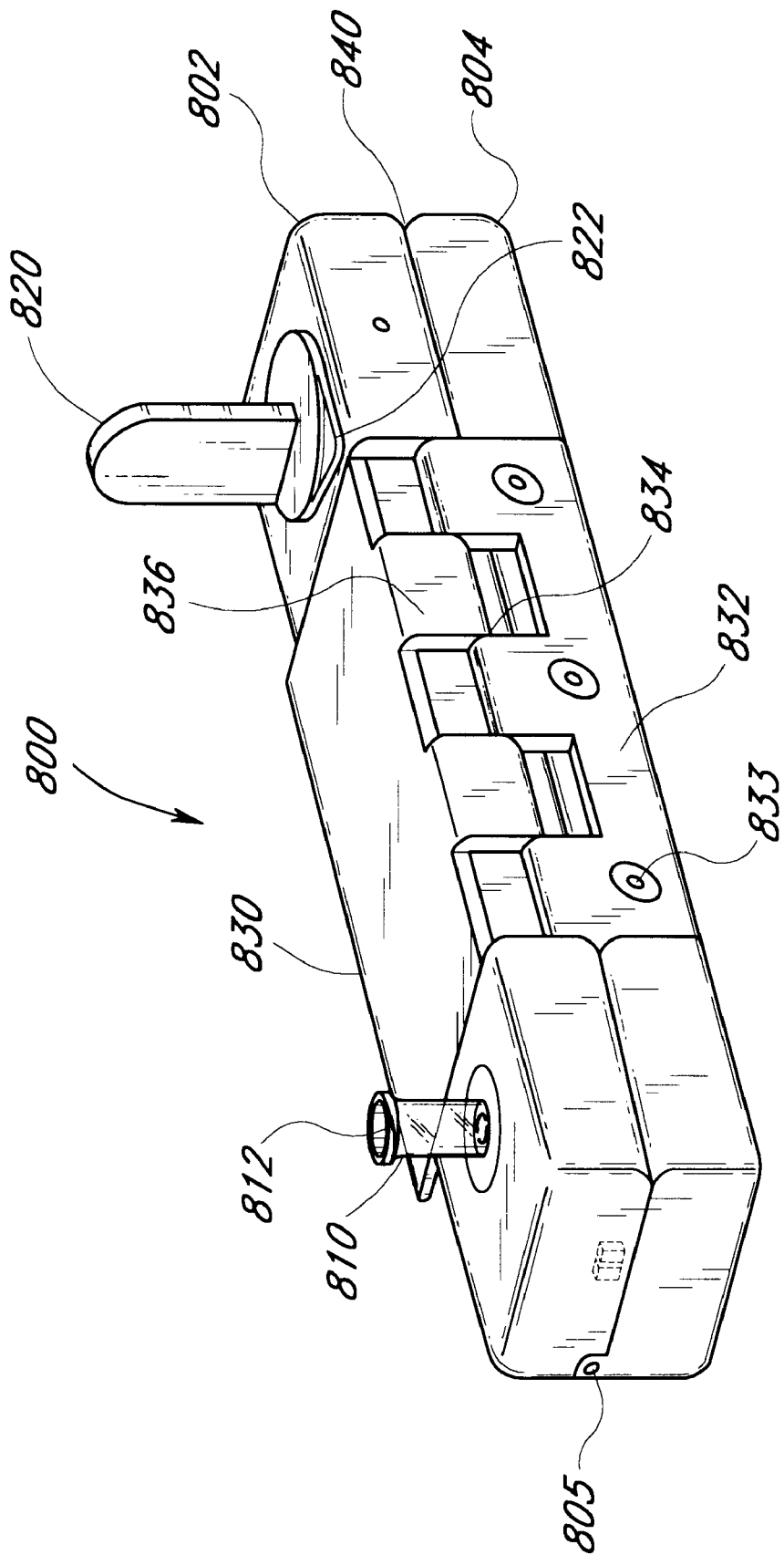
FIG. 16 is a perspective view of an alternative embodiment of an inflation adaptor used to manipulate the low profile valve of the present invention.
Figure 17:
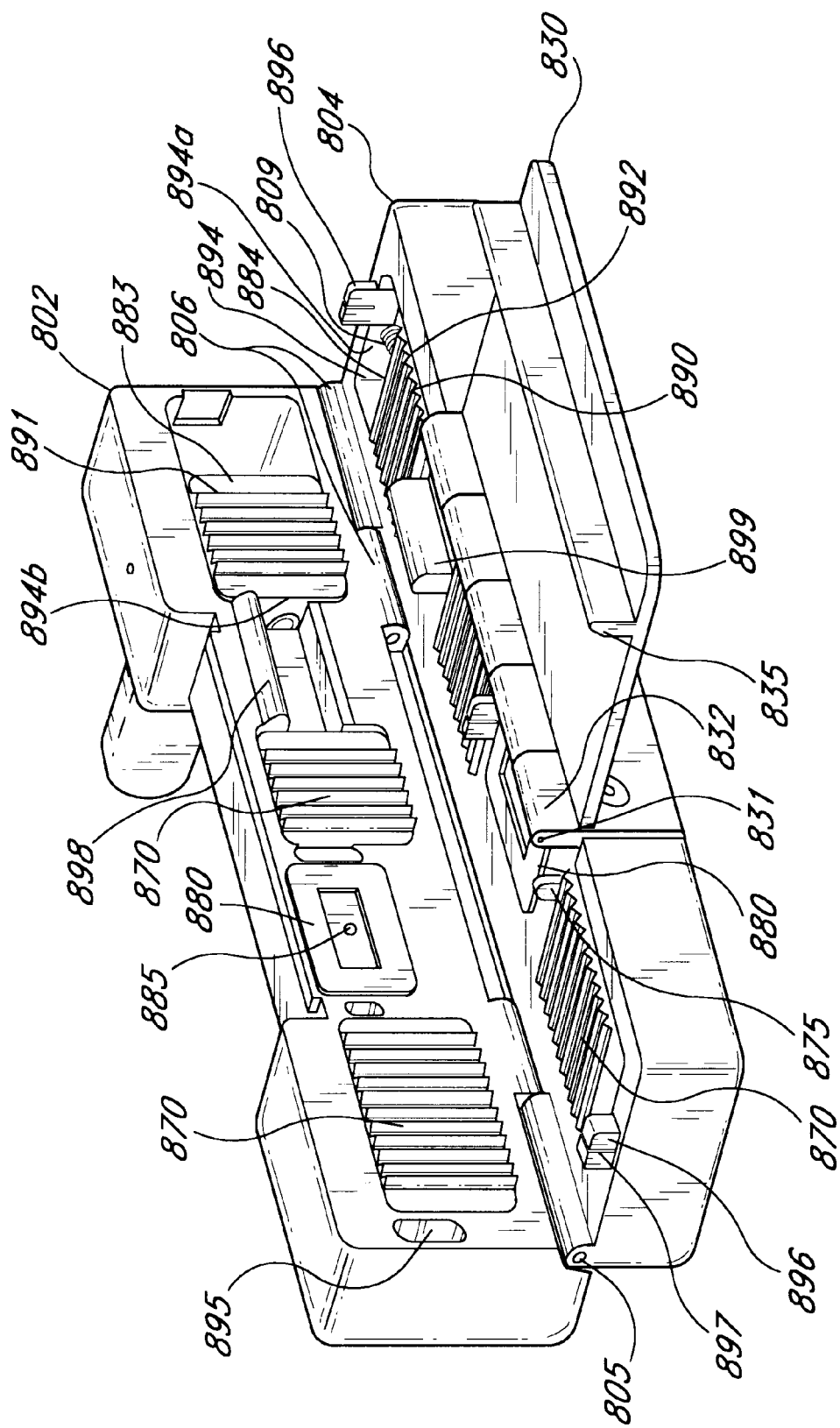
FIG. 17 is a perspective view of the interior of the inflation adaptor of FIG. 16.

Halves 802 and 804 are attached to one another by hinges 806 positioned on one of the lateral edges of each half, through which a joining pin 805 is inserted, such that halves 802 and 804 may be opened or closed in a clam shell manner as depicted in FIGS. 16 and 17. Preferably, the cross-sectional angle formed by halves 802 and 804 in the open position, as shown in FIG. 17, is 90° or greater, and more preferably from 120°–180°, to facilitate insertion of a catheter into adaptor 800.

As shown in FIGS. 16 and 17, a plate 832 is secured to the front portion of housing half 804 by three screws 833. Plate 832 is provided with two or more pin receptacles 834. A cam latch 830 is mounted on plate 832 and is secured thereto by pin 831 which runs through pin receptacles 834 and a corresponding cam latch pin receptacles 836, to form a hinge between cam latch 830 and plate 832. Cam latch 830 and plate 832 may be made from any of the same variety of materials as housing halves 802 and 804, and for any particular embodiment, are preferably made of identical materials, although combinations of materials may also be used. Also, as is appreciated by those of skill in the art, the corresponding hinge structure provided by plate 832 and cam latch 830 may also be achieved by many other methods. For example, plate 832 may be integrally molded with housing half 804 at the time of manufacture as a single piece, thereby eliminating the need for screws 833, but with cam latch 830 mounted thereon as described above.

Cam latch 830 is designed to secure halves 802 and 804 together when adaptor 800 is in use, to assist in the creation of an the inflation seal as described above. Advantageously, by placing cam latch on half 804 as shown, the adaptor interior is more accessible to the clinician during a procedure, and it is easier for the clinician to insert catheters into adaptor 800. Cam latch 830 also serves the important function of preventing accidental opening of the adaptor 800 during use. An important feature of cam latch 830 is the manner in which it cooperates with housing half 802 to create a releasable locking mechanism which applies great force to halves 802 and 804 upon closing, while at the same time using the principles of mechanical advantage to minimize the force the user must exert to close cam latch 830. This is achieved by providing latch 830 with a cammed surface 838 and also providing the front edge of housing half 802 with a rounded lip 837 to accept cammed surface 838, as shown in cross-sectional schematic form in FIGS. 19A–19C.

Figure 19A:
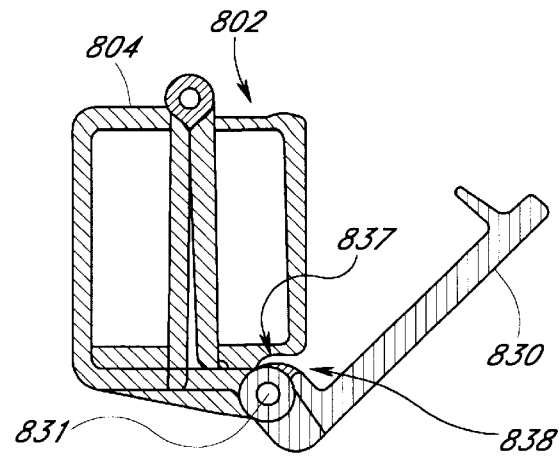
FIGS. 19A–19C are schematic cross-sectional views of the adaptor of FIG. 16, which illustrate the cam locking door mechanism which provides mechanical advantage to the adaptor locking latch.
Figure 19B:
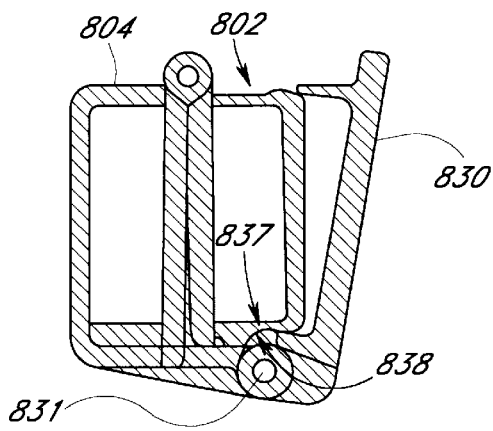
Figure 19C:
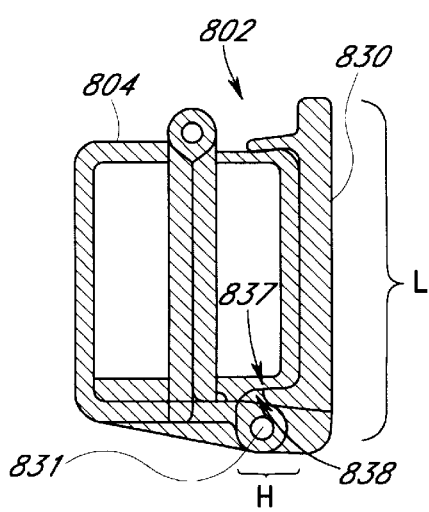

Referring to FIG. 19A, halves 802 and 804 have been brought together, with cam latch 830 in its open position. As cam latch 830 begins to be closed, as shown in FIG. 19B, cammed surface 838 contacts rounded lip 837 and exerts a closing force thereon. Upon further closing, and to the fully closed position shown in FIG. 19C, cam latch 830 acts as a lever, with the closing force between cammed surface 838 and lip 837 being a function of the force of exerted by the user, the length of the lever (length of cam latch door), and the height of the cam surface, as defined by the following well known mathematical equation:

$$F_u = F_c \frac{H}{L}$$

However, as can be appreciated, because the lever length, which in the adaptor embodiment is the length of cam latch 830 in its closing direction, is much greater than the height of the cam created by surface 838 and lip 837, the closing force exerted is always greater than the force the user exerts on cam latch 830. Thus, very tight seals may easily be created by the clinician when the device is used.

Cam latch 830 is also preferably provided with a shelf 835 to secure halves 802 and 804 together. Shelf 835 is positioned on latch 830 at a point such that when latch 830 is in its closed position, shelf 835 firmly contacts housing half 802 along the side bearing hinges 806. Preferably, shelf 835 has an angled leading edge to facilitate closing of latch 830.

A gap 840 separates first half 802 from second half 804 when the halves are closed and latch 830 is secured. Gap 840 is of sufficient width to accept the proximal end of a catheter having the low profile valve of the present invention, as described in detail above, without crimping the catheter to impair its function. A fitting 810 is positioned on half 802, to create an inflation passageway 812 which terminates in opening 885 on the interior surface of first half 802. Fitting 810 is preferably a standard luer connector which may be attached to a variety of existing external pressurized fluid sources, although other types of fittings, such as tubings, quick connects, and Y-site connections, may be easily substituted for a luer fitting.

A seal comprising a pair of gaskets 880 is positioned around opening 885 on the interior surfaces of halves 802 and 804. Gaskets 880 are in alignment, such that when halves 802 and 804 are brought together and secured by cam latch 830, a fluid tight inflation chamber is created within the interior region defined by gaskets 880. The fluid tight inflation chamber is in fluid communication with fitting 810 via inflation passageway 812, so that a pressurized inflation fluid may be introduced into the fluid tight inflation chamber by attaching an external pressurized fluid source to fitting 810. Gaskets 880 are preferably formed of resilient materials, such as silicone, C-Flex(TM) and Pebax(TM) or Kraton(TM), silicone, and other elastomeric materials, so that gaskets 880 may form-fit over a catheter tubular body which extends across the lateral edges of gaskets 880, to create the fluid tight chamber.

An actuator 820 is positioned on the external surface of half 802. In the embodiment illustrated in FIGS. 16–18B, actuator 820 is a rotatable knob controlling a cam which operates a sliding panel 883 on the interior surface of half 802. As will be appreciated by those of skill in the art, however, a great many different actuating structures other than rotatable knobs and sliding panels may be used to achieve the movement of the catheter sealing members described herein. Furthermore, where catheter valves of the present invention require rotational movement, such as those of FIGS. 12 and 13, rotational actuating mechanisms may be provided as well.

Sliding panel 883 moves back and forth along a line which bisects opening 885. When actuator 820 is moved to a first position, shown in FIG. 18A, sliding panel 883 moves away from opening 885 along this line. When actuator 820 is moved to a second position, as shown in FIG. 18B, sliding panel 883 moves toward opening 885 along the same line. A corresponding sliding panel 884 is positioned on half 804, such that panels 883 and 884 are aligned and move together when halves 802 and 804 are closed and the position of actuator 820 is changed.

In actual clinical practice, the movement of panels 883 and 884 results in the opening and closing of a catheter valve placed within adaptor 800. When actuator 820 is moved to the position shown in FIG. 18A, panels 883 and 884 move away from opening 885. This would result in the opening of the valve described in connection with FIGS. 1–5, as the sealer portion of the valve would be positioned proximally of the access port to establish a fluid pathway between the access port and the inflatable balloon at the distal end of the catheter. Conversely, when actuator 820 is moved to the position shown in FIG. 18B, panels 883 and 884 move toward opening 885. This would result in the closing of the valve, as the sealer portion of the valve would be positioned distally of the access port, thereby preventing substantially all fluid flow between the access port and those portions of the catheter distal to the sealer portion. Preferably, detents (not shown) are provided on the actuator camming mechanism to provide the user with tactile and audible feedback when the panels are nearest or farthest from opening 885 (i.e., catheter valve is closed or open, respectively).

Adaptor 800 is also preferably provided with a safety lock, to prevent accidental opening when the adaptor is being used and the catheter valve is open. As shown in FIG. 18A and 18B, this may be achieved by providing an extending flanged portion 822 to actuator knob 820. When actuator knob 820 is in the valve open position, as shown in FIG. 18A, extending flange 822 extends over latch 830, preventing the latch from being opened. In the valve closed position, as shown in FIG. 18B, flange 821 is rotated away from latch 830, which may then be opened.

Panels 883 and 884 each have a roughened surface 890, to facilitate the frictional engagement of panels 883 and 884 and their coordinated travel with the moving portions of the low profile valve. Panels 883 and 884 may be made from any of a variety of polymeric or metallic materials, but must possess sufficient frictional force to engage and move the catheter sealing member without slippage. Consequently, depending on the type of catheter used, those of skill in the art may desire to select different materials for panels 883 and 884 to maximize the frictional forces between the panels and their intended use catheter. In a preferred embodiment, in which panels 883 and 884 are to engage a catheter sealing member made from stainless steel, panels 883 and 884 are both made of Kraton 90A(TM), and roughened surface 890 comprises teeth 891 and grooves 892 formed on each of panels 883 and 884. The teeth 891 and grooves 892 cooperate, to permit the teeth of one panel to fit into the grooves of the opposite panel when the adaptor is closed. Furthermore, alternative cooperating structure, such as dimples and ridges, may also be used to coordinate travel of panels 883 and 884.

One problem that has been recognized with low profile valves of the present invention is the phenomenon of plug walk-out. That is, after the valve has been placed in its closed position, with the sealer portion of the sealing member distal to the inflation access port, and the adaptor removed, the internal forces on the sealing member tend to cause very small portions of the sealing member to be pushed out of the catheter proximal end. Plug walk out is undesirable as it has an adverse impact on the ability of the sealed catheter to act as a guidewire for other devices. It has been found, however, the plug walk out can be minimized or eliminated if the sealing member is initially "overdriven", or forced slightly further in the catheter, during the sealing step.

Advantageously, adaptor 800 is provided with an overdrive system to overdrive a sealing member into a catheter. Referring to FIG. 17, panel 884 travels back and forth within housing recess 894 along a which bisects opening 885, as described above. A spring 809 is mounted in recess 894 and is attached to the wall of recess 894 and panel 884. Spring 809 is biased so as to push panel 884 toward opening 885, and forces panel 884 against the wall of recess 894 which is opposite to that which spring 809 is attached.

Figure 20C:
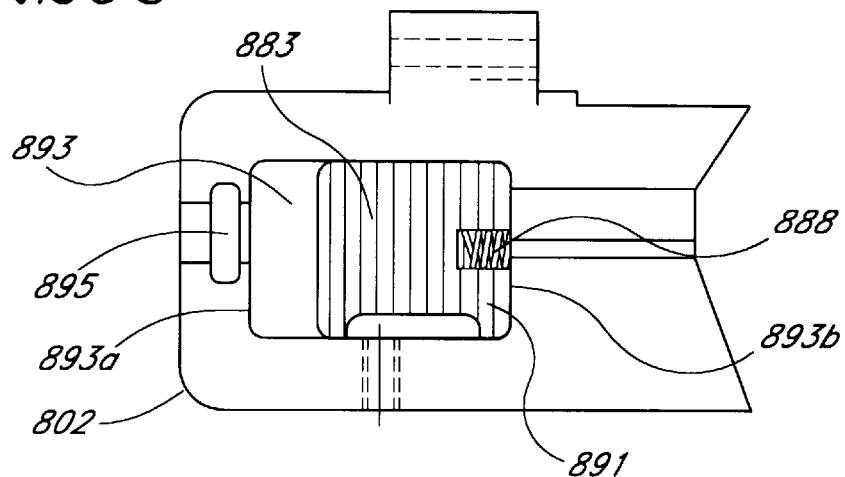
FIGS. 20A–C are close-up views of an embodiment of the adaptor having a sliding top panel biased by a spring mechanism.
Figure 20B:
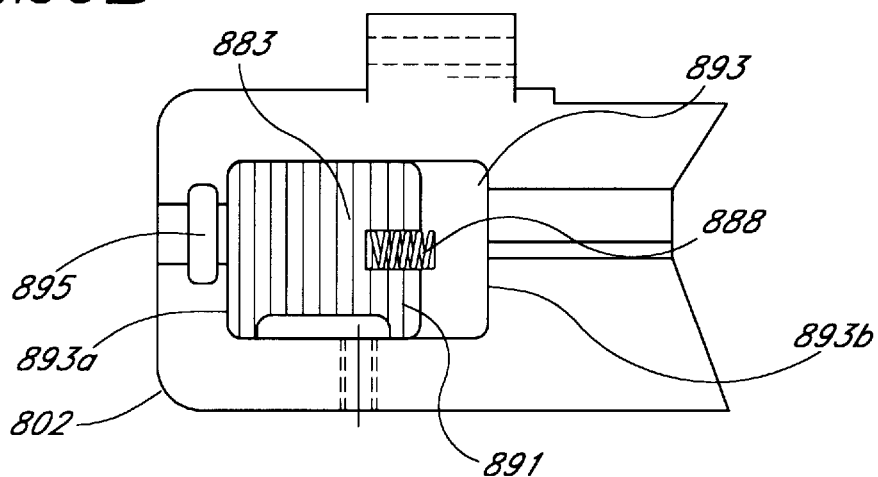
Figure 20A:
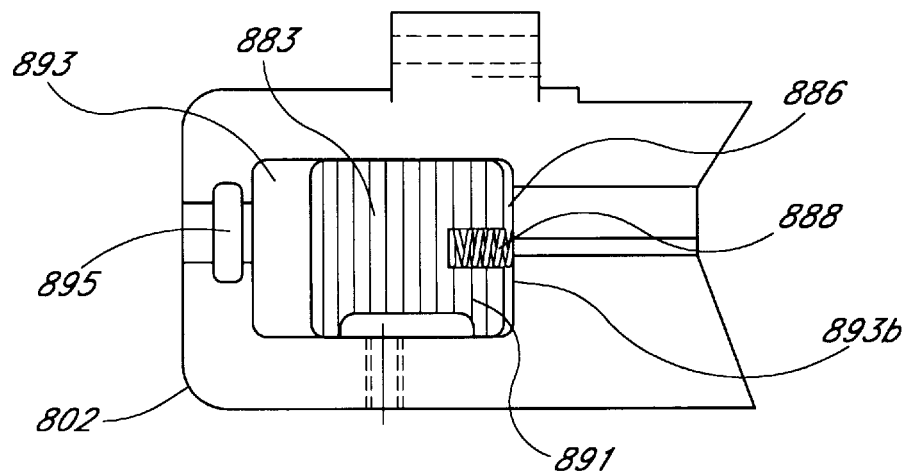

Referring to FIGS. 20A–C, there is shown the top portion of half 802 containing panel 883. Panel 883 resides in housing recess 893, and travels back and forth along a line which bisects opening 885, as described above. The movement of panel 883 is controlled by actuator 820, as described above. An expanded spring 888 is attached to panel 883, as shown in FIGS. 20A–C. Spring 888 has a strength which exceeds that of lower spring 809. In the adaptor open position, as shown in FIG. 17, expanded spring 888 contacts the wall of recess 893, and pushes panel 883 away from the recess wall to create an overdrive gap 886, as shown in FIG. 20A.

When a catheter with a valve in a closed position is loaded into half 804, and halves 802 and 804 are closed and latched, the teeth 891 of panel 883 contact the grooves of panel 884. The superior spring force of spring 888 then forces spring 809 to compress a small amount, such that panel 884 no longer is forced against the recess wall, and now has an overdrive gap (not shown) approximately equal to overdrive gap 886. The actuator may then be engaged to drive panels 883 and 884 away from opening 885 toward recess walls 893a and 894a, respectively, thereby opening the valve mechanism. The inflatable balloon on the catheter may then be inflated as described above.

Upon closure of the valve, by rotating actuator 820 in the opposite direction, panels 883 and 884 are moved toward opening 885 until the sealer portion of the sealing member is distal to the catheter inflation access port. Overdrive of the sealing member is then achieved when actuator 820 is adjusted so that panels 883 and 884 are forced against recess walls 893b and 894b, as shown for panel 883 in FIG. 20C. That is, the force of actuator 820 overcomes the force of spring 888, and drives the sealing member into the catheter by a distance farther than it initially resided before the valve was opened, the distance being approximately equal to the width of gap 886. It has been found that by overdriving the sealing member to a closed position further than its initial closed position compensates for plug walk-out. Preferably, the sealing member is overdriven by a distance of about 0.020 inches.

Alternative overdrive mechanisms may be used for other adaptor embodiments. For example, rather than mounting spring 888 on panel 883, the spring might be mounted in a slot wall 893b, with a plunger (not shown) attached to panel 883 and aligned with the spring. In its unforced state, the spring would exert force on the plunger, pushing panel 883 away from wall 893a to create overdrive gap 896. However, as before, the actuator mechanism 820 could be used to overcome the spring force in the valve closing cycle, thereby creating the overdrive. Numerous other overdrive mechanisms may also be employed, as will be appreciated by those of skill in the art.

As illustrated in FIG. 17, adaptor 800 is also provided with immovable pads 870 on both halves 802 and 804. Pads 870 function to secure the catheter within adaptor 800 when it is closed, and to prevent movement of the catheter during valve opening and valve closing procedures. Accordingly, the material used for pads 870 is selected to have a high degree of frictional force with respect to the surface of the catheter body to which pads 870 will contact. A wide variety of polymeric and metallic materials are thus suitable to form pads 870 such as Kraton(TM), C-Flex(TM) or Pebax(TM). In one embodiment, pads 870 are integrally molded with halves 802 and 804 out of medical grade polycarbonate, and are intended to contact a catheter tubular body formed from nitinol.

It is also preferred that half 804 be provided with guiding means to facilitate correct positioning of the catheter into the adaptor. For the embodiment illustrated in FIG. 17, these guiding means consist of two or more clips 896 to facilitate positioning of a catheter into the adaptor. Clips 896 are provided with grooves 897 in which the catheter is inserted and secured prior to closure of adaptor 800. Clips 896 may be formed of any material flexible enough to be capable of releasably securing the catheters to be used in adaptor 800. In one preferred embodiment, clips 896 are formed of C-Flex 70A(TM). On half 802, and aligned with clips 896, there are provided recesses 895, to accept clips 896 when halves 802 and 804 are brought together and closed. Preferably, alignment indicia on the catheters to be used with adaptor 800 coincide with the spacing of clips 896, so that by placing the catheter portion bearing the indicia directly in clips 896, the catheter is properly inserted in the adaptor with its inflation access port contained in the fluid tight inflation chamber created by gaskets 880 upon closure of adaptor 800. A projecting ridge 875 may also be provided to facilitate placement of the catheter, and direct its orientation during placement in the adaptor so that alignment is proper.

Alternately, other guiding means may be used as well. For example, clips 896 may comprise one or more magnetic elements which cooperate with gold-plated stainless steel rings (or other plated ferromagnetic substances) incorporated into the catheter tubular body to guide the catheter into the correct alignment position.

In one preferred embodiment, as shown in FIG. 17, halves 802 and 804 are also provided with projecting shelves 898 and 899, respectively, which come together when halves 802 and 804 are closed to form a slot therebetween in which the catheter resides. Advantageously, the slot created by shelves 898 and 899 acts to provide reinforcement to a catheter used in adaptor 800 during the valve opening and closing procedures, and helps to prevent buckling or kinking of the catheter tubular body when panels 883 and 884 are moved to open or close the catheter valve.

In clinical practice, there is a direct correlation between the distance that panel 884 moves and the distance moved by the sealer portion of a catheter valve when adaptor 800 is used. Consequently, a controlled and known movement of panel 884 over a set direction and distance results in a movement of the valve sealer portion in the same direction and for substantially the same distance. Thus, with a controlled movement adaptor such as adaptor 800, there is no need to require a catheter having positive cooperating stops to prevent removal of the sealer portion from the catheter, as was described for the catheter of FIGS. 1–5. The adaptor itself prevents accidental withdrawal of the sealer portion from the catheter, by precisely controlling the movement of the sealer portion within the catheter.

Accordingly, in one preferred embodiment, adaptor 800 is used with catheter 900, which lacks positive cooperating stops, and is depicted in FIGS. 21 and 22. Catheter 900 has a tubular body 918 and inflatable balloon (not shown) as described above. Catheter 900 may be formed of materials and methods as described above, and may have structural aspects identical to those described previously, except where otherwise noted.

Catheter 900 has a proximal end 912, and a distal end (not shown) to which is mounted an inflatable balloon. A central lumen 940 extends within tubular body 918 between the proximal and distal ends. An opening 923 to lumen 940 is present at the proximal end 912 of catheter 900. A side-access port 922 in fluid communication with lumen 940 is provided on tubular body 918.

A sealing member 930 is inserted into lumen 940 through central lumen opening 923. Sealing member 930 has a first region 935 which has an outer diameter substantially the same as the outer diameter of the proximal end 912 of catheter tubular body. Region 935 has a taper 934, reducing in diameter to a second region 933 which has an outer diameter less than the inner diameter of lumen 940. Region 933 tapers over length 931 to form a plug mandrel wire 932. As a consequence, region 933 and plug mandrel wire 932 are slidably insertable into the proximal opening 923 of catheter 900 and may freely move within lumen 940. In one preferred embodiment, region 935 has an outer diameter of about 0.013 inches, region 933 has an outer diameter of about 0.0086 inches, and plug mandrel wire has a diameter of about 0.005 inches, with region 933 and plug mandrel wire 932 being inserted into a catheter having a central lumen 940 with an inner diameter of about 0.009 inches.

The length of sealing member region 935 extending proximally of catheter 900 may vary in length depending upon the intended use environment. For example, where catheter 900 is to be used as a guide for other catheters in an "over-the-wire" embodiment, it is preferred that the total length of catheter 900 and sealing member region 935 be about 300 centimeters. Alternately, where catheter 900 is to be used in a single operator or rapid exchange embodiment, it is preferred that the total length of catheter 900 and region 935 be about 180 centimeters. Accordingly, with a known catheter length and use environment, an appropriate length for region 935 may be chosen.

The elements of sealing member 930 may be formed of materials and by methods as described previously. For example, regions 935 and 933 and plug mandrel wire 932 may all be made out of metals such a stainless steel. Alternately, combinations of materials may be used as well. For example, in some applications it may be desirable to manufacture regions 935 and 933 out of stainless steel, while manufacturing plug mandrel wire 932 out nitinol. Furthermore, the various sealing member regions may be made from a single metal wire strand coined at various points to achieve the desired dimensional tolerances, or multiple segments may be joined together to form sealing member 930.

Where multiple segments are joined, region 935, region 933, and plug mandrel wire 932 are attached to one another by any suitable means of bonding metal to metal, such as soldering, brazing, adhesives and the like. In one preferred embodiment, cyanoacrylate adhesives are used to adhere these various parts of sealing member 930 to one another.

As illustrated in FIGS. 21 and 22, the outer diameter of sealing member region 933 is less than the inner diameter of lumen 940, such that region 933 is slidably insertable into lumen 940. In addition, the outer diameters of the tapered portions 931 and wire 932 are also small enough such that they too are slidably insertable in lumen 940. However, the outer diameter of region 935 is greater than the inner diameter 940, and thus only a small portion of tapered portion 934 of sealing member 930 between region 935 and region 933 is insertable into lumen 940 through opening 923. Advantageously, this provides for a snug interference fit when sealing member 930 is fully inserted into catheter 900. This interference fit provides a frictional force which counteracts the tendency of the pressurized fluids and internal wire flexing in the catheter to push sealing member 930 out of opening 923.

As illustrated in FIGS. 21 and 22, sealing member 930 has movement-force increasing structure which increases the force required to move sealing member 930 within lumen 940. The movement-force increasing structure consists of waves 938a and 938b formed in wire 932 near its distal end. Waves 938a and 938b contact the inner surface of lumen 940, thereby increasing the frictional force which must be overcome to move wire 932 within lumen 940. In one preferred embodiment, where wire 932 is made of nitinol and has an outer diameter of about 0.005 inches, and is inserted into a nitinol catheter which has an inner lumen 940 with a diameter of about 0.090 inches, waves are formed on wire 932 for 1½ cycles with an amplitude of about 0.016 inches to increase the valve-opening movement force.

A lumen sealer portion 936 is coaxially and fixedly mounted on wire 932. Sealer portion 936 forms a fluid tight seal with the outer diameter of wire 932 and the inner diameter of lumen 940, such that fluid introduced into lumen 940 through side-access port 922 is prevented from flowing past sealer portion 936 when sealer portion 936 is inserted into lumen 940 distally of side-access port 922. Sealer portion 936 forms the fluid tight seal by firmly contacting the entire inner circumference of a section of lumen 940 along a substantial portion of the length of sealer portion 936, and may be formed of materials and by methods as previously described.

As shown in FIG. 21, sealer portion 936 is positioned proximally of side-access opening 922, so that an unrestricted fluid passageway exists between port 922 and the inflatable balloon at the distal end of catheter 900. This is the valve open position described above. In this position, region 933 is shown partially withdrawn from opening 923. Referring to FIG. 22, sealer portion 936 is positioned distally of port 922, so that fluid flow between port 922 and the inflatable balloon at the distal end of catheter 900 are substantially blocked. This is the valve closed position described above.

Catheter 900 is changed from the valve open position to the valve closed position by the movement of sealing member 930 and its various components. Preferably, the exact length of movement needed to change catheter 900 from the valve closed to the valve open position is built into the movement function of the adaptor used to manipulate sealing member 930 thereby opening and closing the catheter valve. In this regard, it is preferred that catheter 900 be used with an adaptor such as adaptor 800, which provides for such controlled precise movement.

The "stroke-length", or overall movement in one dimension, of sealing member 930 required to open or close the valve may be varied depending upon the catheter requirements. When relying upon the inflation adaptor to control movement, however, it is important that the movement of the controlling elements of the adaptor be coordinated with those of sealing member 930. With respect to adaptor 800, this is accomplished by selecting a recess 893 dimension which precisely defines the distance that sealing member 930 is to travel to achieve the valve open and valve closed positions, without accidentally removing sealing member 930 from opening 923. In one embodiment, where access port 922 is positioned 36 mm from opening 923, a stroke length of 5.5 mm was found to be suitable.

In a further embodiment, a balloon-on-a-wire device 401 incorporating the present invention is shown in FIGS. 23 and 24. The device 401 consists of a guide wire 402 formed of a suitable material such as stainless steel and having a suitable diameter as for example ranging from 0.010" to 0.032" but preferably a diameter ranging from 0.014" to 0.018". It is preferable that the guide wire 402 be formed of a nickel titanium alloy typically called Nitinol which has the advantage that it is more flexible and has greater kink resistance characteristics than another suitable material such as stainless steel.

It has a suitable length as for example 150 cm. The guide wire 402 is provided with proximal and distal extremities 403 and 404 and is provided with a central lumen 406 extending from the proximal extremity to the distal extremity. The lumen can be of a suitable size as for example 0.010" I.D. for an 0.014" O.D. guide wire. An occlusion balloon 411 is coaxially mounted on the distal extremity 404 of the guide wire 402.

A removable inflation fitting 441 or valve attachment 441 is mounted on the proximal extremity of the guide wire 402 and forms a part of the balloon-on-a-wire device 401. The fitting or attachment 441 is formed of a suitable material such as a polycarbonate and is provided with a central bore 442. The attachment or fitting is slid externally over the proximal extremity 403 of the guide wire 402. Means is provided for forming a fluid-tight seal between the proximal extremity 403 of the guide wire 402 and a body 443 of the fitting 441 and consists of an o-ring 446 (see FIG. 25) seated in a well 447. A thumb screw 448 is threadedly mounted on the body 443 and is provided with an inwardly extending circular protrusion 449 that is adapted to engage the o-ring 446 and to compress the same to form a fluid-tight seal when the protrusion 449 is moved inwardly toward the o-ring 446 as the thumb screw 448 is rotated in a clockwise direction. The o-ring 446 decompresses or springs back when released upon rotation of the thumb screw 448 in a counterclockwise direction so that the fitting 441 can be removed from the distal extremity 403 of the guide wire 402. The body 442 also includes a Luer fitting 451 which provides an inflation port 452 that is in communication with the bore 442 in the body 443 and which is also in communication with the open proximal extremity of the guide wire 402 and the lumen 406 therein.

Means is provided for plugging the bore 406 when the removable attachment or fitting 441 is removed and consists of a plug mandrel 456 formed of a suitable material such as 0.014" stainless steel solid rod. It is necessary that this rod have a diameter which is greater than the diameter of the lumen 406 and the guide wire 402. The plug mandrel 456 is provided with a progressive portion 456a that tapers down from as, for example from 0.014" to a suitable diameter as for example 0.008" to a cylindrical portion 456b.

Means is provided for forming a fluid-tight seal between the plug mandrel 456 which forms a plug mandrel and the body 443 of the attachment or fitting 441 and consists of an o-ring 466 providing suitable sealing means seated within a well 462 provided in the body 443. A thumb screw 463 threadedly engages the body 443 and is provided with a cylindrical protrusion 464 which engages the o-ring and compresses it to form a fluid-tight seal with respect to the plug mandrel 456 by rotation in a clockwise direction of the thumb screw 463. The plug mandrel 456 can be released by a counterclockwise rotation of the thumb screw 463 permitting decompression of the o-ring 461.

The occlusion balloon 411 can be readily inflated by use of a syringe secured to the fitting 451 of the removable valve fitting or attachment 441 of the balloon-on-a-wire device 401 and accessible outside the body of the patient. Now let it be assumed that the occlusion balloon 411 has been inflated and that it is desired to introduce a therapeutic balloon catheter 501 into a working space to treat a stenosis. This can be readily accomplished in the present invention by inserting a plug mandrel 456 into the open end of the lumen 406 of the guide wire 402. After the plug mandrel 456 has been inserted, the syringe can be removed after which the thumb screws 448 and 463 can be loosened to permit the o-rings therein to become decompressed and to release the guide wire 402 and the plug mandrel 456 to permit the fitting or valve attachment 441 to be slipped off to provide a proximal end on the core wire 402 which is free of obstructions. During removal of the valve attachment or fitting 441, the occlusion balloon 411 remains inflated and continues to be disposed distally of the stenosis 482.

It will be appreciated that certain variations of the present invention may suggest themselves to those skilled in the art. The foregoing detailed description is to be clearly understood as given by way of illustration, the spirit and scope of this invention being limited solely by the appended claims.

What is claimed is:

1. An intravascular guidewire inflation system, comprising:
    a hollow metallic body having distal and proximal portions, said body having a central lumen formed therein with distal and proximal ports in fluid communication with said lumen;
    an expandable member mounted on said distal portion of said body and adapted to be in fluid communication with said distal port of said central lumen, such that fluid introduced through said proximal port will cause actuation of said expandable member;
    a valve movably inserted with respect to said proximal port of said body, said valve movable between a first position to seal said central lumen to prevent deactuation of said expandable member and a second position to unseal said central lumen to allow actuation or deactuation of said expandable member; and
    a valve adaptor which may be removably mounted on said proximal portion of said body, said adaptor having an auxiliary lumen adapted to be in fluid communication with said proximal port of said central lumen and further adapted to receive a fluid delivery device for selectively actuating or deactuating said expandable member, said adaptor having a first seal to engage said metallic body at a point distal to said proximal port, and a second seal to engage said valve, such that when said first and second seals are engaged on said distal point and said valve, a fluid tight sealing chamber is established surrounding said proximal port.

2. The guidewire inflation system of claim 1, wherein said metallic body comprises nitinol.

3. The guidewire inflation system of claim 1, wherein said expandable member comprises a balloon formed from an elastomeric material selected from the group consisting of C-Flex, silicones, latex and polyurethanes.

4. The guidewire inflation system of claim 2, wherein said metallic body has an outer diameter of from about 0.010 inches to about 0.032 inches.

5. The guidewire inflation system of claim 4, wherein said metallic body has an outer diameter of from about 0.014 inches to about 0.018 inches.

6. A surgical guidewire inflation system, comprising:

a hollow metallic body having distal and proximal portions, said body having a central lumen formed therein with distal and proximal ports in fluid communication with said central lumen;

an inflatable member mounted on said distal portion of said body in fluid communication with said distal port of said central lumen, such that fluid introduced through said proximal port will cause inflation of said inflatable member;

a valve movably inserted with respect to said proximal port of said body, said valve movable between a first position to seal said central lumen to prevent deflation of said inflatable member and a second position to unseal said central lumen to allow inflation or deflation of said inflatable member; and a valve adaptor which may be removably mounted on said proximal portion of said body, said adaptor having an auxiliary lumen adapted to be in fluid communication with said proximal port of said central lumen and further adapted to receive a fluid delivery device for selectively inflating or deflating said inflatable device, said adaptor having a seal to engage said metallic body, thereby creating a fluid tight seal between said auxiliary lumen and said proximal port.

7. The guidewire inflation system of claim 6, wherein said metallic body comprises nitinol.

8. The guidewire inflation system of claim 6, wherein said inflatable member comprises a balloon formed from an elastomeric material selected from the group consisting of C-Flex, silicones, latex and polyurethanes.

9. The guidewire inflation system of claim 7, wherein said metallic body has an outer diameter of from about 0.010 inches to about 0.032 inches.

10. The guidewire inflation system of claim 6, wherein said metallic body has an outer diameter of from about 0.014 inches to about 0.018 inches.

11. The guidewire inflation system of claim 6, wherein said distal portion of said hollow metallic body comprises a coil at the distal tip of said body.

12. The guidewire inflation system of claim 11, wherein said central lumen has a core wire inserted therein at a distal opening, and said core wire extends distally from said distal opening within said coil.

13. The guidewire inflation system of claim 6, wherein said valve comprises a metallic rod slidably inserted into said central lumen.

14. The guidewire inflation system of claim 13, wherein the diameter of a first portion of said metallic rod is less than the internal diameter of said central lumen and the diameter of a second portion of said metallic rod is greater than the diameter of said central lumen.

15. The guidewire inflation system of claim 14, wherein the diameter of said second portion of said metallic rod is about 0.014 inches or less.

16. A method of inflating a balloon mounted on a hollow surgical guidewire during a medical procedure, comprising the steps of:

providing a hollow guidewire having a proximal end and a distal end with a central lumen extending therethrough, and a proximal opening and a distal opening, said distal opening being in fluid communication with said central lumen, said guidewire further having an inflatable balloon mounted near said distal end, said inflatable balloon being in fluid communication with said distal opening and said lumen, said central lumen further having a valve member inserted therein at said proximal end, said valve member being movable to at least a first position and a second position, and wherein said proximal opening is in fluid communication with said distal opening when said valve member is in the second position but not when said valve member is in the first position;

introducing said guidewire into a patient;

attaching a releasably securable inflation adaptor to said proximal end of said guidewire such that said proximal opening is contained within a sealing member of said inflation adaptor;

forming a fluid tight inflation chamber over said proximal opening by closing said sealing member about said proximal end; and introducing a pressurized inflation fluid into said fluid tight inflation chamber, wherein said inflation fluid enters said proximal opening and said central lumen and inflates said balloon.

17. The method of claim 16, further comprising moving said valve member to said first position and detaching said adaptor from said proximal end, wherein said balloon remains inflated.

18. The method of claim 17, further comprising deflating said balloon comprising the further steps of:

attaching said adaptor to said proximal end;

forming said fluid tight inflation chamber over said proximal opening by closing said sealing member over said proximal end; and moving said valve member from said first position to said second position, such that inflation fluid may exit said balloon through said proximal opening.

19. The method of claim 18, further comprising securing a vacuum apparatus to said adaptor and applying negative pressure to said fluid tight inflation chamber to deflate said balloon.

20. A surgical guidewire inflation system, comprising:

an elongate hollow body having distal and proximal portions, said body having a lumen formed therein with distal and proximal openings in fluid communication with said lumen;

an inflatable member mounted on said distal portion of said body in fluid communication with said distal opening of said lumen, such that fluid introduced through said proximal opening causes inflation of said inflatable member;

a movable sealing member for sealing said proximal opening of said hollow body; and an adaptor having an inflation inlet for inflating said inflatable member, said adaptor being removably mountable on said proximal portion of said body such that fluid introduced into said inflation inlet flows into said proximal opening to inflate said balloon, said sealing member being movable within said adaptor to seal said proximal opening and maintain inflation of said inflatable member upon removal of said adaptor from said proximal portion of said body.

* * * * *

UNITED STATES PATENT AND TRADEMARK OFFICE
CERTIFICATE OF CORRECTION

PATENT NO. : 6,050,972

DATED : April 18, 2000

INVENTOR(S): Zadno-Azizi et al.

It is certified that error appears in the above-identified patent and that said Letters Patent is hereby corrected as shown below:

At item [75], please delete the following names from the list of inventors: April A. Marano-Ford, Jefferey C. Bleam, Isaac J. Kim, Jeffrey E. Field, Roy Leguidleguid, Mukund Patel and George Tsai.

Figure 9A on drawing sheet 5 of 16 should be replaced with Figure 9A as originally filed in the application.

At column 25, line 62, please replace "896" with --886--.

Signed and Sealed this

Twenty-fourth Day of April, 2001

*Attest:*

NICHOLAS P. GODICI

*Attesting Officer*   *Acting Director of the United States Patent and Trademark Office*